US010842925B2

(12) United States Patent
Kant et al.

(10) Patent No.: US 10,842,925 B2
(45) Date of Patent: *Nov. 24, 2020

(54) LOW RESISTANCE MICROFABRICATED FILTER

(71) Applicant: THE REGENTS OF THE UNIVERSITY OF CALIFORNIA, Oakland, CA (US)

(72) Inventors: Rishi Kant, Foster City, CA (US); Shuvo Roy, San Ramon, CA (US); Benjamin Chui, Sunnyvale, CA (US); Kenneth G. Goldman, Olmsted Falls, OH (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/353,919

(22) Filed: Mar. 14, 2019

(65) Prior Publication Data

US 2019/0269841 A1 Sep. 5, 2019

Related U.S. Application Data

(63) Continuation of application No. 14/400,288, filed as application No. PCT/US2013/041428 on May 16, 2013, now Pat. No. 10,265,452.

(Continued)

(51) Int. Cl.
*A61M 1/16* (2006.01)
*B01D 39/16* (2006.01)
(Continued)

(52) U.S. Cl.
CPC ....... *A61M 1/1621* (2014.02); *B01D 39/1692* (2013.01); *B01D 61/145* (2013.01);
(Continued)

(58) Field of Classification Search
CPC .................................................. A61M 1/1621
See application file for complete search history.

(56) References Cited

U.S. PATENT DOCUMENTS

| 5,798,042 A | 8/1998 | Chu et al. |
| 7,655,075 B2 | 2/2010 | Hofmann |
| (Continued) | | |

FOREIGN PATENT DOCUMENTS

| JP | 2002531246 | 9/2002 |
| JP | 2004209632 | 7/2004 |
| (Continued) | | |

OTHER PUBLICATIONS

Kuiper et al. (1998) "Development and applications of very high flux microfiltration membranes" Journal of Membrane Science 150(1): 1-8.

(Continued)

*Primary Examiner* — Peter Keyworth
(74) *Attorney, Agent, or Firm* — Edward J. Baba; Shweta Chandra; Bozicevic, Field & Francis LLP

(57) ABSTRACT

The present technology provides micro fabricated filtration devices, methods of making such devices, and uses for microfabricated filtration devices. The devices may allow diffusion to occur between two fluids with improved transport resistance characteristics as compared to conventional filtration devices. The devices may include a compound structure that includes a porous membrane overlying a support structure. The support structure may define a cavity and a plurality of recesses formed in a way that can allow modified convective flow of a first fluid to provide improved diffusive transport between the first fluid and a second fluid through the membrane.

14 Claims, 19 Drawing Sheets

Related U.S. Application Data

(60) Provisional application No. 61/647,939, filed on May 16, 2012.

(51) Int. Cl.

| | | |
|---|---|---|
| *B01D 67/00* | (2006.01) | |
| *B01D 69/02* | (2006.01) | |
| *B01D 69/10* | (2006.01) | |
| *B01D 61/14* | (2006.01) | |
| *B01D 63/08* | (2006.01) | |
| *B01D 69/06* | (2006.01) | |
| *C23F 1/00* | (2006.01) | |
| *B01D 61/02* | (2006.01) | |
| *B01D 61/24* | (2006.01) | |

(52) U.S. Cl.
CPC .......... *B01D 61/147* (2013.01); *B01D 63/08* (2013.01); *B01D 63/087* (2013.01); *B01D 67/006* (2013.01); *B01D 67/0058* (2013.01); *B01D 69/02* (2013.01); *B01D 69/06* (2013.01); *B01D 69/10* (2013.01); *C23F 1/00* (2013.01); *B01D 61/027* (2013.01); *B01D 61/243* (2013.01); *B01D 2239/0654* (2013.01); *B01D 2239/10* (2013.01); *B01D 2239/1216* (2013.01); *B01D 2315/14* (2013.01); *B01D 2325/02* (2013.01); *B01D 2325/021* (2013.01); *B01D 2325/08* (2013.01); *B01D 2325/26* (2013.01)

(56) References Cited

U.S. PATENT DOCUMENTS

| | | |
|---|---|---|
| 2001/0047959 A1 | 12/2001 | Oishi |
| 2004/0219072 A1 | 11/2004 | Yamakawa et al. |
| 2006/0278580 A1 | 12/2006 | Striemer et al. |
| 2007/0039471 A1 | 2/2007 | Hofmann |
| 2009/0029142 A1 | 1/2009 | Jacobson |
| 2009/0252971 A1 | 10/2009 | Saha et al. |
| 2010/0147762 A1 | 6/2010 | Zhang et al. |
| 2011/0009799 A1* | 1/2011 | Mullick .............. A61M 1/3672 604/6.14 |
| 2011/0108473 A1 | 5/2011 | Friedberger et al. |
| 2011/0143232 A1* | 6/2011 | Burban ................ B01D 53/228 429/414 |

FOREIGN PATENT DOCUMENTS

| | | |
|---|---|---|
| JP | 2008540070 | 11/2008 |
| JP | 2009513317 | 4/2009 |
| WO | 2005/023404 | 3/2005 |
| WO | 2006/127256 | 11/2006 |
| WO | 2011/040868 | 4/2011 |
| WO | 2012/039645 | 3/2012 |

OTHER PUBLICATIONS

Baker (2004) "Topography Control Using Sacrificial Capping Layers", Solid State Technology, Pennwell Corporation, vol. 47, No. 8, pp. 33/34, 36.

Donnelly, et al. (2013) "Plasma Etching: Yesterday, Today, and Tomorrow", Journal of Vacuum Science & Technology A: Vacuum, Surfaces, and Films, pp. 050825-050848.

Han (1999) "Novel Fabrication and Characterization Method of Fabry-Perot Microcavity Pressure Sensors", Sensors and Actuators A: Physical, Elsevier BV, NL, vol. 75, No. 2, pp. 168-175.

Turner, et al. (1998) "Monolithic Nanofluid Sieving Structures for DNA Manipulation", Journal of Vacuum Science & Technology B: Microelectronics and Processing and Phenomena, American Vacuum Society, pp. 3835-3840.

\* cited by examiner

LOW RESISTANCE MICROFABRICATED FILTER

TECHNICAL FIELD

The present technology relates to filtration devices and methods of making and using filtration devices. More specifically, the present technology relates to making and using microfabricated filters.

BACKGROUND

Filtration devices are used in a variety of ways to provide purified materials. As technology improves, sensitive processes may require highly purified materials to be provided, and thus improved filters may be required. Micro and nanofabrication may be used to produce fine mesh filters for use in such processes. However, as filter dimensioning decreases, manufacturing issues such as brittleness and performance issues such as breakdown may increase. Additionally, as filter pore dimensions decrease, pressure gradients may increase above useable thresholds. Accordingly, there is a need for improved filtration devices and methods of making such devices. These and other needs are addressed by the present technology.

SUMMARY

Microfabricated filters according to the present technology may include a planar membrane section including a plurality of pores. Each pore of the plurality of pores may have a width of less than or about 100 nm. The devices may further include a support section including a substrate coupled with the membrane section. The substrate may include a plurality of thick portions and a plurality of recesses between the thick portions and a second thin portion that is between adjacent thick portions. The recesses may be in communication with the pores in the plurality of pores. The thin portion of the substrate may be characterized by a thickness of between about 10 μm and about 100 μm. The thin portion may also be characterized by thicknesses of between about 20 μm and about 50 μm. The microfabricated filtration device may further include an additional layer of material between the substrate and the membrane section. In disclosed embodiments, the additional layer of material may include a dielectric material.

Methods of using microfabricated filtration devices are also described. The methods may include delivering the fluid to a filtration device, and the filtration device may include a planar membrane section including a plurality of pores. Each pore of the plurality of pores may have a width of less than or about 100 nm. The device may further include a support section including a substrate coupled with the membrane section. The substrate may include a plurality of thick portions and a plurality of recesses between the thick portions and a second thin portion that is between adjacent thick portions. The recesses may be in communication with the pores in the plurality of pores. The methods may further include flowing the fluid over the planar membrane section to produce a filtered fluid. The methods may still further include delivering the filtered fluid from the filtration device. The filtration device may further include a first channel in fluid communication with the membrane section of the filtration device, and a second channel in fluid communication with the support section of the filtration device. The methods may further include flowing the first fluid through the first channel in a first direction of flow. The methods may also include flowing a second fluid through the second channel in a direction of flow that is countercurrent to the first direction of flow. The methods may further include transporting solutes across the membrane section between the first fluid and the second fluid. The methods may still further include pumping the first and second fluid through the filtration device to maintain equal pressure across the membrane section of the filtration device. The methods may also include incorporating an additional material into the first fluid prior to delivering the fluid to the filtration device.

The disclosed technology further encompasses microfabricated filtration devices having a membrane section having a thickness of less than about 1 μm in height, and defining a plurality of pores having a width of less than about 10 nm. The filtration devices may further include a support section including a substrate coupled with the membrane section, where the substrate at least partially defines a cavity and a plurality of recesses. The cavity may be located within the backside of the substrate and may be in communication with the plurality of recesses, where the recesses are in communication with the defined pores. Additionally, the plurality of recesses may be defined by portions of the substrate such that each portion of the substrate located between any two recesses comprises a height of about 50 μm or less. The support section of the filtration devices may further include at least one additional layer of material disposed between the substrate and membrane sections, where the at least one additional layer may define a portion of the recesses. The portions of the substrate located between any two recesses may be characterized by a height of about 20 μm or more. The plurality of recesses may be characterized by a diameter of less than about 150 μm. The substrate of the microfabricated filtration device may be characterized by a single homogenous layer of material. The cavity defined in the microfabricated filtration device may include inwardly sloping walls toward the plurality of recesses. The plurality of recesses within the microfabricated filtration device may be characterized by length by width measurements of about 100 μm by about 50 μm.

Additional methods of making microfabricated filtration devices are also disclosed. The methods may include depositing a dielectric layer over a semiconductor substrate. The methods may additionally include forming a first layer of a membrane material on the dielectric layer and etching a pattern in the first membrane material layer. The methods may also include forming a sacrificial dielectric layer over the patterned first membrane material layer, and forming a second membrane material layer over the sacrificial dielectric layer. The methods may also include forming a protective layer over the second membrane material layer. The methods may further include etching the substrate with a first etchant process that produces a cavity that does not extend to the layers of membrane material. The methods may also include etching the substrate with a second etchant process that forms a plurality of recesses through the remaining portion of the substrate. The methods may also include etching the filtration device with a third etchant process that removes the sacrificial dielectric layer forming pores through the membrane material layers, which provides access to the recesses such that the combination of the pores, recesses, and the cavity produce apertures through the filtration device. The first etching process may include a wet etchant in disclosed embodiments, and in disclosed embodiments the first etchant process and the second etchant process may include a reactive ion etch.

Additional methods of filtering fluid are also encompassed by the technology, and may include delivering a first fluid into a filtration device. The methods may further include flowing the first fluid across the front side of a filtration member located in the filtration device that includes a membrane section having a thickness of less than about 1 μm in height, and defining a plurality of pores having a width of less than 10 nm. The methods may also include flowing a second fluid across the backside of the filtration member located in the filtration device that includes a support section comprising a substrate coupled with the membrane section, with the substrate at least partially defining a cavity and a plurality of recesses. The cavity may be located in the backside of the substrate and may be in communication with the plurality of recesses, where the recesses are in communication with the defined pores. The plurality of recesses may be defined by portions of the substrate such that each portion of the substrate located between any two recesses may be characterized by a height of about 50 μm or less. The second fluid may flow through the cavity to provide the second fluid to the recesses such that solute transport may occur across the membrane section between the first and second fluids to produce filtered first fluid. The methods may further include transferring the filtered first fluid from the filtration device.

Such technology may provide numerous benefits over conventional techniques. For example, improved filtration may be provided based on the reduced thickness of the filtration pores produced in the disclosed devices. Additionally, reduced manufacturing queue times may be afforded by the fabrication processes described. These and other embodiments, along with many of their advantages and features, are described in more detail in conjunction with the below description and attached figures.

BRIEF DESCRIPTION OF THE DRAWINGS

An understanding of the nature and advantages of the disclosed technology may be realized by reference to the specification and drawings.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

The present technology provides microfabricated filtration devices, methods of making such devices, and uses for microfabricated filtration devices. In one example, the filtration devices may allow diffusion to occur between two fluids with improved transport resistance characteristics as compared to conventional filtration devices. The devices may include a compound structure that includes a membrane overlying a support structure. The support structure may define a cavity and a plurality of recesses formed in a way that can allow modified convective flow of a first fluid to provide improved diffusive transport between the first fluid and a second fluid through the membrane.

Figure 1:
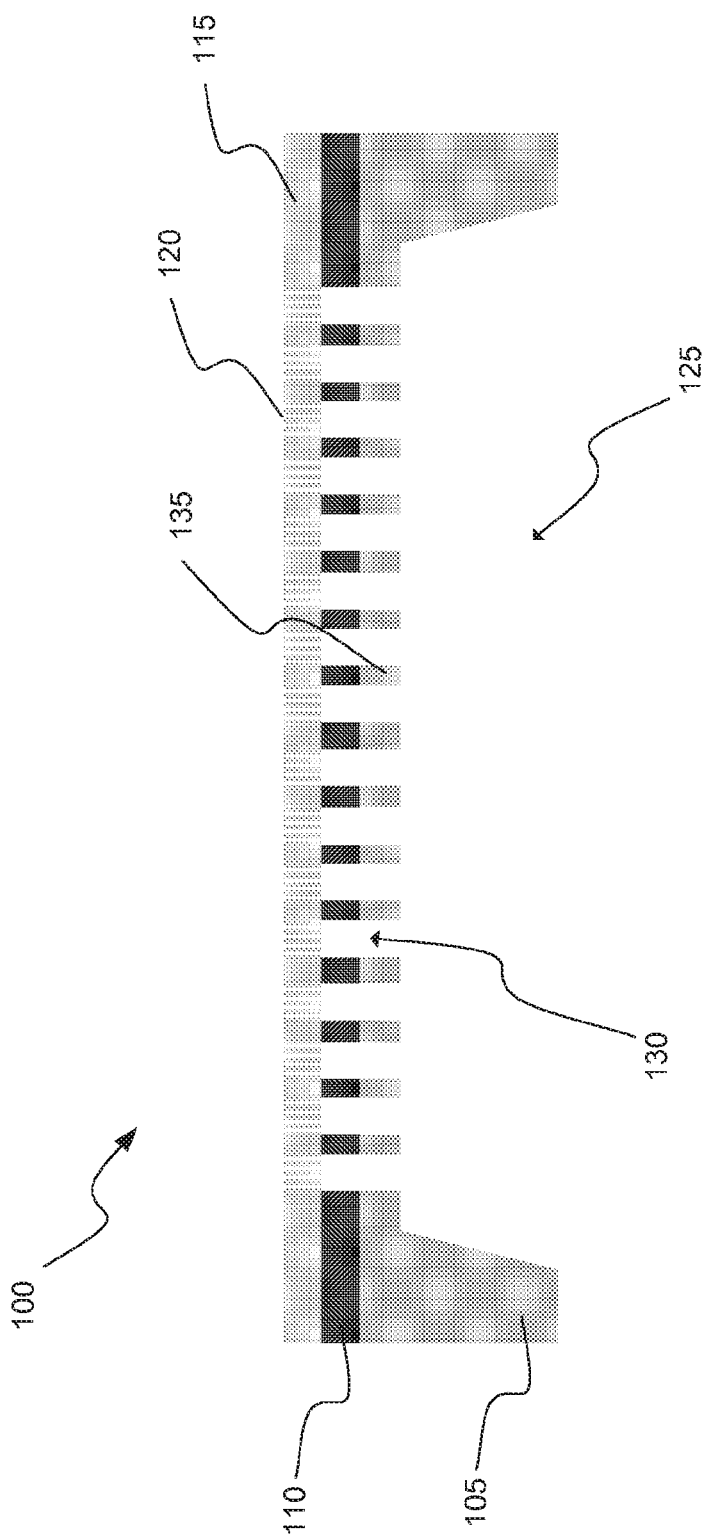
FIG. 1 shows a cross-sectional view of a filter fabricated according to embodiments of the present technology.

FIG. 1 shows a cross-sectional view of a microfabricated filter 100 fabricated according to embodiments of the present technology. The filter 100 includes a membrane section 115 overlying a substrate section 105. The filter may include one or more additional layers 110 between the membrane section 115 and substrate section 105 in various configurations. For example, an additional layer 110 may be included that acts as an etch stop layer during fabrication, a protective coating, a structural member to provide extra rigidity or flexibility, etc. The additional layers may be of the same or a different material as the membrane or substrate layers.

The substrate section 105, which may act as a support section for the membrane 115, may be a silicon wafer as is conventionally used in microfabrication, and may be, for example, a silicon wafer that may have a variety of crystal orientations including a [100] plane orientation as listed by the Miller indices. The substrate may be a 100 mm diameter silicon wafer having a thickness of 400 μm, but can also be larger or smaller diameters including about 76 mm or smaller, or about 150 mm, about 200 mm, about 300 mm, about 450 mm, etc., or larger. Additionally, the thickness of the wafer may be based on convention for the diameter of the wafer, but may also be less then about 400 µm, about 600 µm, about 700 µm, about 900 µm, etc. or more. The substrate may additionally be germanium, Group IV elements of the periodic table, III-V compounds including gallium arsenide, II-IV compounds including zinc tellurium, p and n doped compounds, etc.

The membrane section 100 may be formed with any number of materials that can be deposited or grown on a micro- or nano-thick scale on a substrate 105 or intermediate layer 110. For example, the membrane material may be made with silicon, polysilicon, silicon carbide, ultrananocrystalline diamond, diamond-like-carbon, silicon dioxide, PMMA, SU-8, PTFE, titanium, silica, silicon nitride, polytetrafluorethylene, polymethylmethacrylate, polystyrene, silicone, or various other materials. The additional layer or layers 110 may include a dielectric material such as a nitride or oxide layer, including silicon nitride for example, as well as flexible materials including elastomers or materials providing strength and/or rigidity to the filter structure, including metals, ceramics, and polymers.

Among the final stages of fabrication may include the production or formation of pores 120, which may be produced by the removal of a sacrificial material, for example, from the membrane section 115, which may include a planar membrane. The pores may be of various shapes including linear, square, circular, ovoid, elliptical, or other shapes. In some embodiments, the plurality of nanofabricated pores have a width less than 100 nm, e.g., less than or about 50 nm, 20 nm, 15 nm, 10 nm, 7 nm, 5 nm, 3 nm, etc., or less. In some embodiments, the distance, e.g., average distance, between each of the plurality of nanofabricated pores may be less than about 500 nm, and may be less than or about 50 nm, 100 nm, 150 nm, 200 nm, 250 nm, etc., or more. In some embodiments, the length of the nanofabricated pores may be less than about 200 µm, and may be less than 100 µm, 50 µm, 40 µm, 30 µm, 10 µm, etc., or less. In some embodiments, the plurality of nanofabricated pores have a slit shape. In some embodiments, the membrane 115 comprises more than one pore, where the pores comprise a single shape or any combination of shapes. In some embodiments, a membrane comprises more than one pore, where the pore sizes range from about 10 to about 100 µm in any dimension; the dimensions need not be the same in any particular pore shape, and the pores may comprise a single size or any combination of sizes. Additionally, the pores may be lined up from membrane to membrane, or offset from one another in various fashion across or within membranes. The pore size formed may be dictated by the process for which the filtration device may be utilized. For example, if the device is used for diffusion in a dialysis process, the pores may be able to allow for diffusion of ions and nutrients, but may substantially prevent the flow of albumin and cellular material through the membrane.

During the fabrication of the filters, apertures may be formed that may include the pores 120, as well as a plurality of recesses 130 that are in communication with the pores, and one or more cavities 125. The apertures may be formed to provide access to the membrane structure from the backside of the filter, i.e., through the substrate 105, and may be formed to produce an array of functioning membranes 115 as will be described in more detail below. The apertures may include a cavity 125 through which a fluid may be transported. The cavity 125 provides access to a plurality of recesses 130 that are separated by divisions 135 that may be formed by portions of the substrate 105, and may be thin portions of the substrate as compared to the thicker support sections defining the lower parts of the cavity, as well as any intermediate or additional layers 110 that are located above the substrate 105. The substrate may include a thicker portion located nearer the backside of the substrate, as well as a thinner portion located nearer the front side of the substrate. The thicker portion may define the cavity 125 across the substrate, while the thinner portion may define the plurality of recesses 130 located between the thick portion defining the cavity 125 and the membrane 115. When a fluid is flowed through the cavity 125, the filtration device may allow for diffusive transport across the membrane section 115 through the pores 115 and recesses 130. The cavity 125 may have walls that slope towards the diffusive recesses as shown in the Figure. Such sloping may provide improved flow characteristics, by providing a more streamlined flow of a fluid forced across the structure, although in other embodiments the structure may have more square walls or shapes. By providing the cavity, several benefits may be provided including reducing the resistance through the diffusive recesses, and being able to provide a refreshed fluid more often across the recesses. For example, the filtration device may be used during a fluid filtration process including hemodialysis that may involve diffusion and/or ultrafiltration. By reducing the diffusive resistance, less membrane surface may be needed as will be explained below. Additionally, by improving the flow of fluid across the substrate, the refresh rate of the fluid being used may be improved.

Figure 2A:
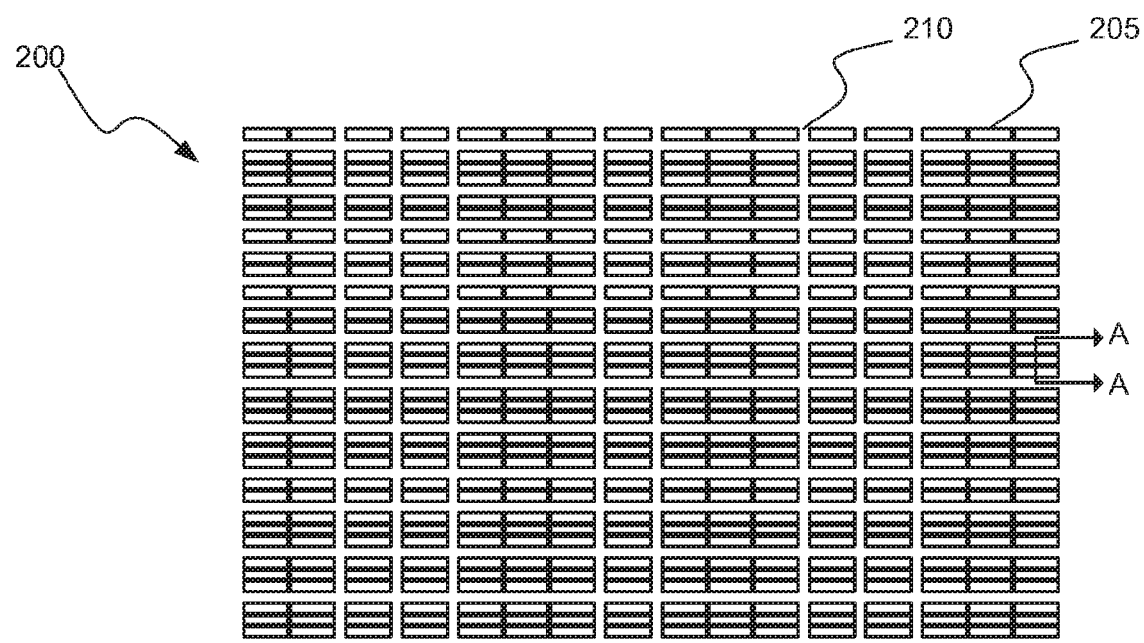
FIG. 2A shows a top view of an array of membranes as may be disposed on a support structure according to embodiments of the present technology.

FIG. 2A shows a top view of an array 200 of membranes 205 as may be disposed on a support structure according to embodiments of the present technology. The array may include various configurations of membranes 205 separated by dividers 210. The dividers 210 may provide several benefits including anchoring the pores located across the membranes, as well as providing structural support to the membrane 205 as a whole. The membrane structures 205 may be patterned over an area of a substrate that may include lengths as small as several microns, or as large as several millimeters. In some embodiments, the entire surface of the substrate may be patterned with the membrane structure, while alternatively less than the entire surface may be patterned to improve uniformity in thickness or configuration, for example.

Figure 2B:
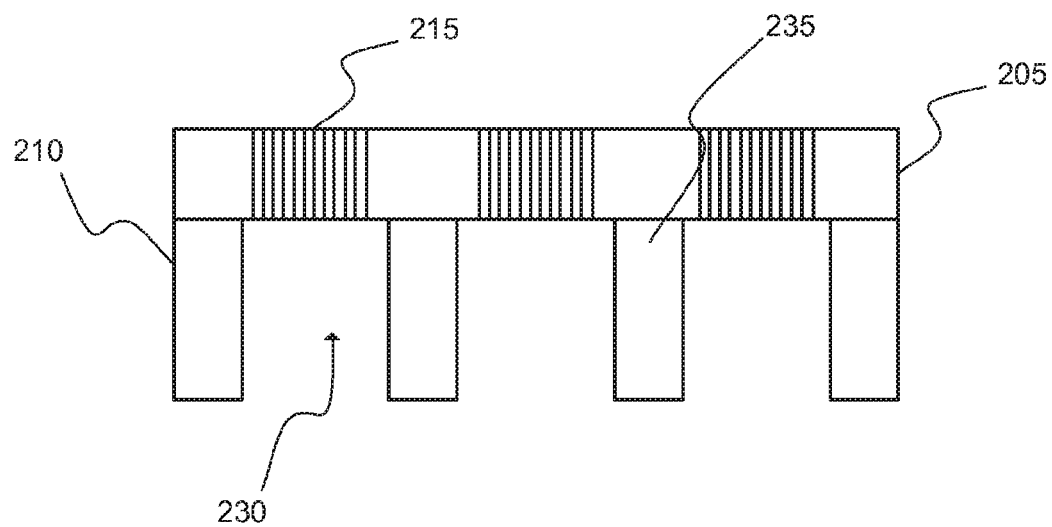
FIG. 2B shows a cross-sectional view along lines A-A of FIG. 2A of a filter fabricated according to embodiments of the present technology.

FIG. 2B shows a cross-sectional view along lines A-A of FIG. 2A of a filter fabricated according to embodiments of the present technology. This sectional view is not necessarily to scale, nor as would necessarily be located along the periphery of a substrate. In some embodiments a greater or fewer number of layers may be incorporated, for example, including an etch stop layer. This view is intended to aid one of skill in conceptualizing the structure of an embodiment of the filtration device without limiting the scope of the technology disclosed herein. The cross-section shows the location of apertures 215 formed through the membrane sections 205. In practice, the apertures may be formed in a pattern or array on the underside of the substrate to provide access through the membrane surface. The apertures 215 may be of any shape or size, and may be formed at particular intervals along the substrate to produce useable membranes at specific locations to provide a determined area of filtration across the device. The apertures may be formed as sections including one or more pores through the membrane, a diffusive recess, and a cavity. Exemplary recesses may have a diameter of less than or about 500 µm, with diameter referring to a straight line passing from side to side of any figure regardless of actual shape. For example, a rectangular recess may be formed with lengths less than 500 µm each. Recesses may be of any shape or dimensions, including square, rectangular, circular, elliptical, etc., or other geometric figures, and may reach to the limits of the substrate dimensions. Exemplary recesses may be rectangular, and may comprise side lengths less than or about 400 µm, 300 µm, 200 µm, 100 µm, 75 µm, 60 µm, 50 µm, 40 µm, 30 µm, 20 µm, 10 µm, etc. or less. In one embodiment the recesses are rectangular and have length by width dimensions of about 120 µm by 60 µm. Alternative recesses may have dimensions of 100 µm by 50 µm, or less, and may include other combinations as would be understood by one of skill. The dimensions of a recess may depend on several variables including the pressure that may be applied to or across the membrane, the material used for the membrane section, etc. Recesses formed in filtration devices according to embodiments of the present technology may be smaller than can some conventional recesses due to the increased permeability that may be produced by the structure of the device. This feature will be explained in still greater detail below.

The exemplary support structure 210 as can be seen in the cross-sectional view does not show the cavity located below the remaining support structures 210 formed across the structure and providing access to the diffusive recesses 230. The recesses 230 may be separated by dividers 235 that include portions of the substrate. The dividers 235 provide structural support to the membrane 205, while also defining the diffusive recesses 230 through which transportation can occur. As can be appreciated by the view of FIG. 2, although the entire surface of the filtration device may be structured with the membrane section 205, the functional portions of the membrane may be defined by the areas under which the recesses are formed. The process of forming recesses under the membranes provides the paths or apertures through which transportation can occur. The process for forming apertures will be described below with reference to FIGS. 3A-3F.

FIGS. 3A-3F show cross-sectional views of a filter during certain steps of a method for making a filter according to embodiments of the present technology. As described previously, and shown in FIG. 3A, a substrate 305 may be provided on which the membranes are formed. In one example, the substrate is a silicon substrate having a diameter of about 100 mm and a thickness of about 400 µm, although substrates of differing materials and dimensions can be used to equivalent effect. A protective oxide or nitride layer 310 may be deposited over the substrate. The layer 310 may include a silicon nitride, silicon oxide, silicon oxynitride, silicon carbide, or some other layer of material including other dielectric materials and combinations. For example, multiple layers of oxide, a combined layer of oxide and nitride, etc., may form layer 310. Additionally, multiple layers may be grown or deposited in combination for layer 310. The thickness of the protective layer 310 may be about 5 µm in one example.

Alternatively, the protective layer may be less than or about 10 µm, 7 µm, 4 µm, 3 µm, 2 µm, 1 µm, 500 nm, 400 nm, 300 nm, 200 nm, 100 nm, 50 nm, 10 nm, etc., or less. The protective layer 310 may be deposited by CVD including LPCVD and PECVD, or by some other deposition means. For example, the protective layer may be grown with a thermal process. Onto this protective layer may be deposited a first membrane material layer 315 such as polysilicon, in one example. The first membrane material may be deposited by the same or a different deposition means, and may include LPCVD in one example. The thickness of the first membrane material layer may be about 5 µm in one example. Alternatively, the first membrane material layer 315 may be less than or about 10 µm, 7 µm, 4 µm, 3 µm, 2 µm, 1 µm, 750 nm, 500 nm, 450 nm, 400 nm, 350 nm, 300 nm, 250 nm, 200 nm, 150 NM, 100 nm, 50 nm, 25 nm, 10 nm, etc., or less. In still another embodiment, the substrate used may be a silicon-on-insulator (SOI) and a protective layer may not be additionally deposited over the existing material of the substrate.

Figure 3A:
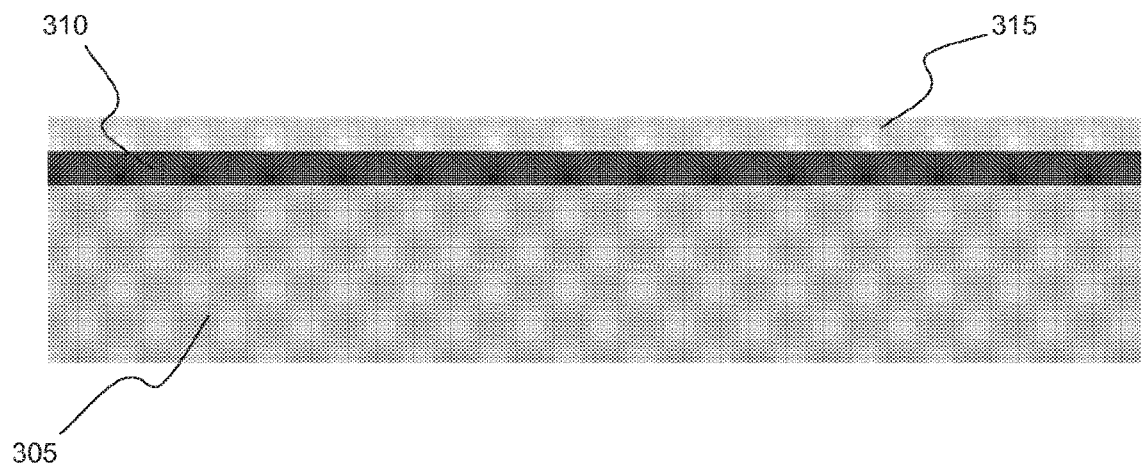
FIGS. 3A-3F show cross-sectional views of a filter during certain steps of a method for making a filter according to embodiments of the present technology.
Figure 3B:
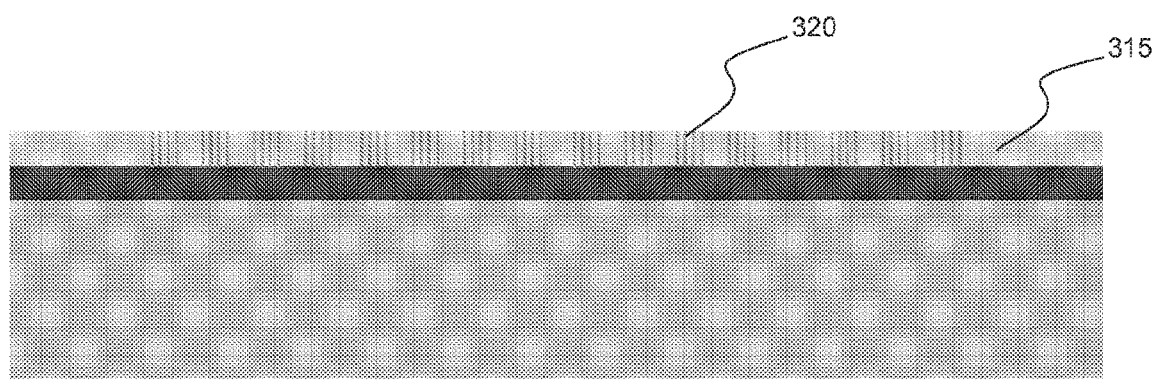

FIG. 3B shows the formation of a pore structure in the membrane material layer. The pore structure may be formed with a sacrificial material that may be later removed to form pores through the membrane material. The pore structure 320 may be formed with an etching process, or other lithography process. The first membrane material layer 315 may be patterned with a photoresist that may be performed via e-beam, deep ultraviolet lithography, or another patterning technique that can form patterning for creating structures as described herein. The resist pattern may be transferred via a reactive ion etch or wet etch process onto the first membrane material layer 315. Following the patterning, a sacrificial layer of material may be formed on or within the patterned first membrane material layer 315. The sacrificial layer may be an oxide grown via thermal oxidation that may be less than 20 nm thick. Alternatively, the layer may have a thickness of less than or about 15 nm, 10 nm, 7 nm, 5 nm, 3 nm, 1 nm, 5 angstrom, etc., or less. The layer of material may be conformal when grown, and thus the film may be formed via a more conformal process including HDPCVD, or some other conformal deposition process. The layer may be silicon oxide, or any other material that can be subsequently removed from the membrane section to create the pores.

The layer of sacrificial material may be selectively removed in certain areas with a subsequent photoresist patterning and etch. This may provide areas for anchoring a second membrane material layer to the first membrane material layer during a subsequent deposition. After removing the photoresist, a second membrane material may be deposited filling in the anchor cavities, as well as the areas around the sacrificial layer in and around the trenches formed in the first membrane material. This material may be the same or a different membrane material as previously described. For example, the second membrane material may also be polysilicon. The second membrane material layer may be about 5 µm in one example. Alternatively, the protective layer may be less than or about 4 µM, 3 µm, 2 µm, 1 µm, 750 nm, 600 nm, 500 nm, 400 nm, 300 nm, 200 nm, 100 nm, 50 nm, 10 nm, etc., or less. The second membrane material layer may be planarized down at least to a level exposing the sacrificial material, and thereby forming the pore structure 320. The planarization may occur with any polishing or etching technique, and can include a reactive ion etch in one example. In still another example, the anchors may be formed and filled subsequent to depositing the second membrane material and performing a planarization. The process may alternatively be performed by performing an additional lithography step followed by a direct etching, such as with a reactive ion etch, followed by a specific deposition for the anchor material.

The pores may also be more densely patterned by performing a series of patterning and deposition processes. For example, subsequent to the initial deposition of the membrane material, a secondary patterning step similar to that as described above may be performed. Once the secondary patterning has been performed, an additional protective layer may be deposited in a way as previously described. Following the formation of the additional protective layer, a subsequent layer of membrane material may be formed to provide the degree of pore spacing required. The repetitive processing may reduce the line and space pattern by 20% or more. Alternatively, the repetitive processing can reduce the line and space pattern by about 30% or more, about 40%, about 50%, about 55%, about 60%, about 65%, about 70%, about 75%, about 80%, about 85%, about 90%, etc., or more. In one example, by performing a subsequent series of patterning and formation, an initial patterning process of 450 nm line/space pattern can be reduced to 150 nm or less. By maintaining the protective material within the pores during fabrication, pore integrity may be maintained until a final release is performed.

Figure 3C:
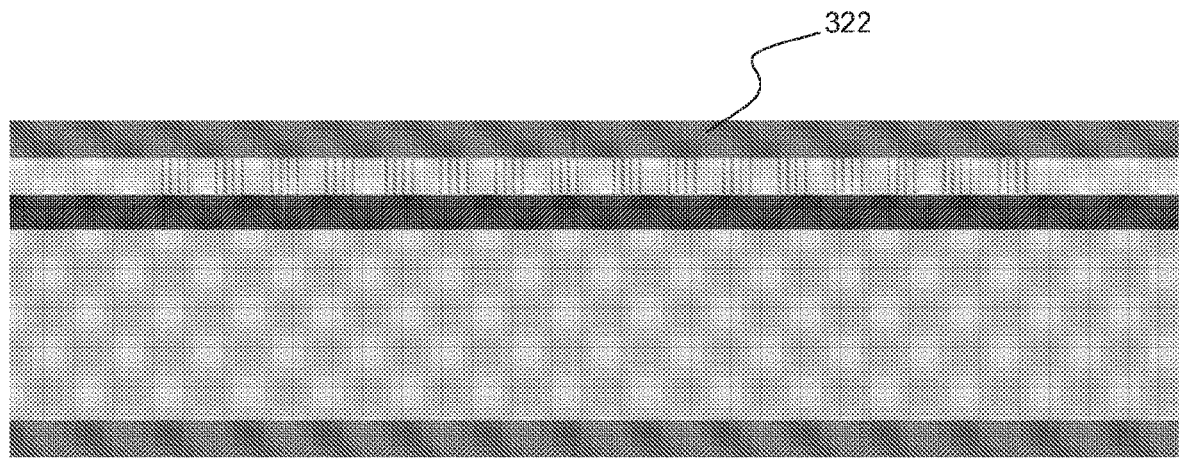

FIG. 3C shows that a second protective layer 322 is applied over the membrane materials 315 prior to the backside processes. The second protective layer may include an oxide, nitride, or another compound depending on the etching technique subsequently performed. For example, a nitride layer may be deposited if a potassium hydroxide etch is performed, and an oxide layer may be deposited if the subsequent etch includes a chemical selective to nitrogen, such as tetramethylammonium hydroxide.

Figure 3D:
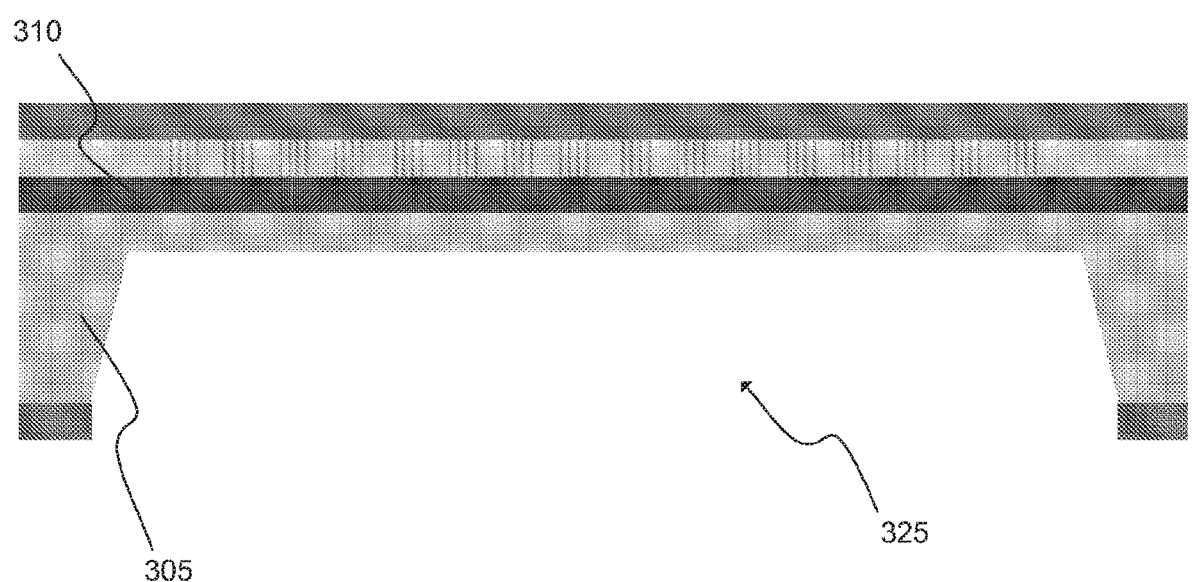

FIG. 3D shows a first etchant process that can be performed on the backside of the filtration device. A cavity 325 may be etched through the substrate 305 that may not remove material to the level of the first protective layer 310. The first etchant may be a wet etchant, that may be, for example, potassium hydroxide, tetramethylammonium, buffered hydrofluoric acid, EDP, etc. The determination of when to stop the etch process can be based on a desired thickness of remaining substrate. The first wet etch may be isotropic or orientation selective, i.e., anisotropic. As shown in FIG. 3D, in an exemplary first etch process, KOH is used to produce sloped sides of the substrate 305 for the convective cavity. Because certain etchants including KOH, EDP, and TMAH display an etch rate selective to [100] orientation over [111] orientations, sloped walls can be produced defining the convective cavity. In other embodiments, etchants can be used that are more anisotropic and produce little or no sloping of the cavity walls. Additionally, a reactive ion etch may be performed for the first etchant process. Additionally, multiple cavities can be formed across the bottom of the substrate. In some examples, cavities are etched asymmetrically across the substrate. A plurality of cavities etched may have the same or different dimensions. In one example, relatively square cavities may be etched that may be about 1 mm per side or more. Alternatively the cavities may be about 2 mm per side, about 3 mm, about 5 mm, about 7 mm, about 10 mm, about 12 mm, about 15 mm, about 17 mm, about 20 mm, etc., or more. Alternative geometries having any of the dimensions per side as described herein can also be etched as cavities in the substrate.

Figure 3E:
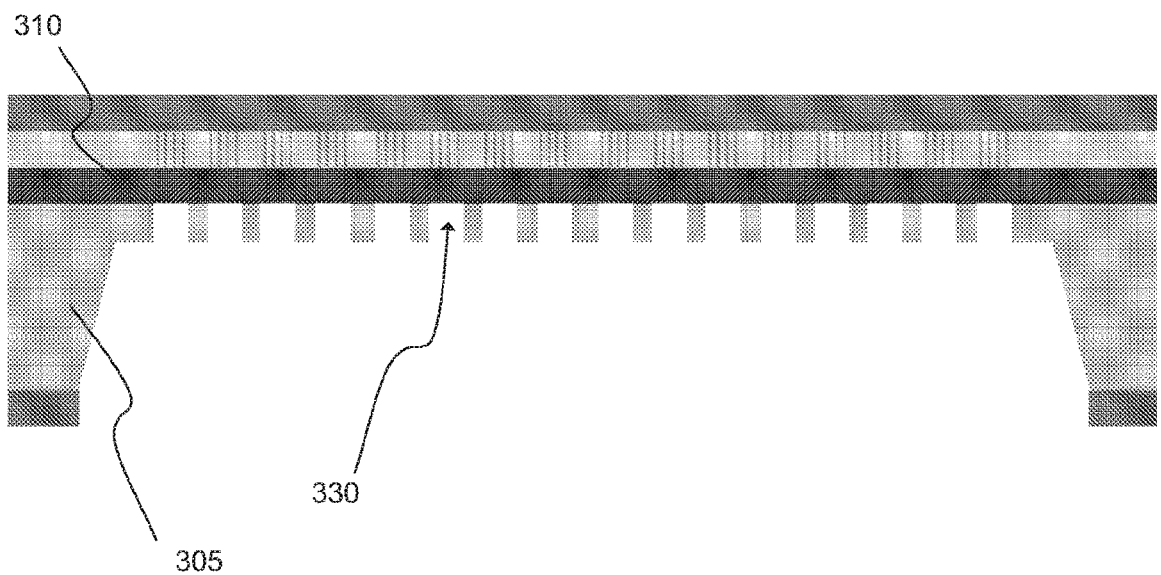

Following the formation of the cavity 325, patterning can be formed on the backside of the substrate in order to form the desired recesses 330 as illustrated in FIG. 3E. The patterning can be formed on the remaining exposed substrate at the top portion of the cavity 325. The patterning can create windows of any of the shapes and dimensions as previously described through which the etching of the recesses may be performed. For example, windows of 100 µm by 50 µm may be formed in various patterns across the bottom of the substrate for the formation of diffusive recesses. In an alternative example, the windows may be 250 µM by 50 µm. Depending on the size of the substrate, many such windows can be formed depending on the dimensions and the width of material left between the windows. For example, on a 100 mm diameter substrate, more than 20,000 windows or more could be patterned that are roughly 100 µm by 50 µm. A certain amount of substrate may be provided between each window in order to provide structural support for the membrane when exposed. The amount of substrate left between each window may be less than or about 100 µm on each side. Alternatively, the amount of substrate left between each window may be less than or about 80 µm, 70 µm, 60 µm, 50 µm, 40 µm, 35 µm, 30 µm, 25 µm, 20 µm, 17 µm, 15 µm, 12 µm, 10 µm, 7 µm, 5 µm, 3 µm, 1 µm, 500 nm, etc., or less. The windows may also be formed in other patterns based on the dimensions of the cavity formed. For example, if a cavity is etched by the process described within a 10 mm square area, and the windows have dimensions of about 250 µm by 50 µm, for example. The area may provide fewer than 1000 windows in one example. Alternatively, the area may provide more than about 1000 windows, about 1200, about 1300, about 1500, about 1700, about 2000, about 2300, about 2500, about 2700, about 3000, about 3500, etc. or more.

The etching to form the diffusive recesses may be a dry etch process, and may include reactive ion etching or a Bosch or other deep etching process. The etching may be performed to the level of the first protective layer 310 originally deposited over the substrate 305 surface, thereby using the material as an etch stop layer. After the etching is complete, the height of the diffusive recesses may be less than about 100 µm. Alternatively, the height of the diffusive recesses may be less than or about 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, etc., or less. Alternatively still, the height of the diffusive recesses may be greater than or about 1 µm 2 µm, 3 µm, 5 µm, 10 µm, 15 µm, 20 µm, 25 µm, 30 µm, 35 µm, 40 µm, 45 µm, 50 µm, 55 µm, 60 µm, etc., or greater. In still another alternative, the height of the diffusive recesses may be between about 0 µm and 400 µm, 0 µm and 300 µm, 0 µm and 200 µm, 0 µm and 100 µm, 10 µm and 80 µm, 10 µm and 60 µm, 20 µm and 60 µm, 20 µm and 50 µm, 30 µm and 50 µm, etc. By maintaining the height of the diffusive recesses 330 greater than about 20 µm or more, improved structural integrity may be produced that may affect membrane integrity during both fabrication and utilization of the filtration device membranes.

Figure 3F:
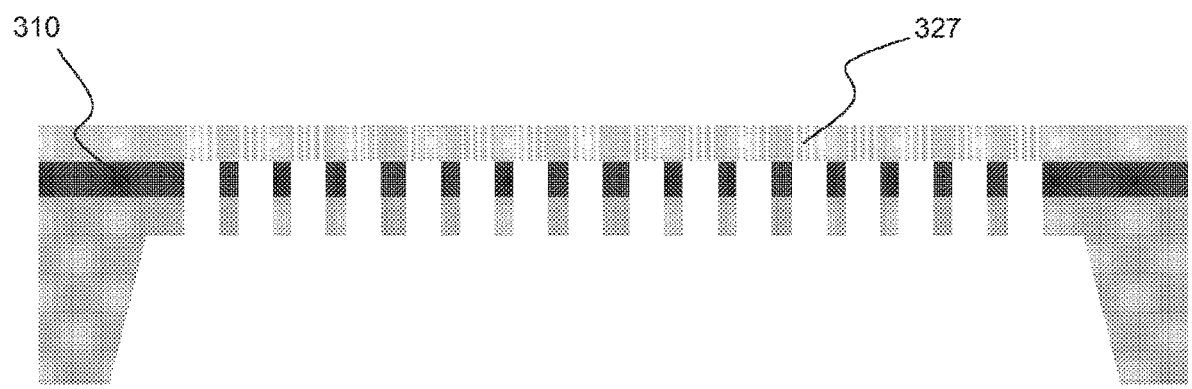

FIG. 3F shows an exemplary resultant filter after a third etch process is performed. After the diffusive recesses have been formed, mechanical processes including chip dicing may be performed. The diced chips may be of any dimension, and may be based on the dimension of the cavities formed in the substrate and the amount of space between successive cavities. For example, each chip may be 10 mm square. This dimensioned chip includes a cavity of less than 10 mm square, and a plurality of windows. The sized substrates may then be etched with a third etchant to remove the second protective layer 322, as well as the portions of the first protective layer 310 that have been exposed as a result of the second etch process forming the recesses. Additionally, the third etchant may include multiple etchants optimized for the particular materials sought to be removed. For example, if both a nitride and oxide layer are sought to be removed, a phosphoric acid wash followed by a hydrofluoric acid wash may be performed. Once these layers have been removed, the third etchant may also remove the sacrificial material of the pore structures 320 in order to expose the pores 327, which complete the apertures. The resultant filtration devices may then be utilized for filtration purposes. The third etchant may be, for example a wet etchant, and may be an etchant capable of dissolving each of the protective layers and sacrificial layers. In one example, a hydrofluoric acid may be used.

After the chips are diced and the pores are exposed, filters may be developed with one or more membrane chips. For example, a filter may be composed of a single chip. Alternatively, a number of chips may be combined in various ways to produce a filter with a greater surface area of membrane available. Chips may be combined laterally or vertically in various formations. In one example, a series of chips may be stacked in alternately opposing formation to produce channels between two membranes. A series of parallel channels may be formed in this way, and a filter may be composed of a plurality of these channels. The spacing of a channel may be defined by the spacing between the two membranes. In one embodiment, the spacing may be about 1000 µm between two membranes forming a channel of equivalent width. Alternatively, the channel formed may be greater than 1000 µm in width. In still alternative examples, the spacing may be less than about 1000 µm in width, and may be less than about 800 µm, about 600 µm, 500 µm, 400 µm, 300 µm, 250 µm, 200 µm, 150 µm, 100 µM, 50 µm, 10 µm, 1 µm, 800 nm, 600 nm, 500 nm, 400 nm, 300 nm, 250 nm, 200 nm, 150 nm, 100 nm, 50 nm, etc., or less.

The number of chips stacked laterally, and the number of channels created vertically may vary depending on the amount of active membrane surface area required for a specific filter. For example, filters may be formed that have more or less effective surface area based on the number of chips included in the filter. The number of chips used in the filter may be determined by the required dimensions of the filter, or by the required effective surface area of the filter. In one exemplary filter, channels having a length of a single chip are formed. The channels may include alternately opposing orientations such that every two membranes are directed towards each other, and the interposing chips are directed with the membranes away from each other, i.e., the backside of the chips face each other. For example, a filter having two such primary channels may include four chips. A primary channel for a first fluid may be formed by the spacing between the membrane side of the chips, and a secondary channel for a second fluid may be formed by the spacing between the backside of two chips. With an exemplary four chips, two primary channels divided by one secondary channel may be formed. Other filters may include more or less than 3, 4, 5, 6, 7, 8, 9, 10, 12, 14, 16, 18, 20, 50, 75, 100, 150, 200, etc. or more channels. Additionally, the number of chips may be based on the required surface area for filtration. For example, if roughly 0.1 square meters of filtration membrane area is required, this can be developed from a few or several dozen chips organized laterally and/or vertically. Alternatively, the same effective surface area of membrane material can be presented by laterally increasing the number of chips. For example, a primary channel can be created with four chips, with two chips laterally disposed and facing another two chips laterally disposed. Many other combinations of chips/channels can be formed, and one of skill can appreciate that a virtually limitless set of channel/chip combinations can be made to develop filters of almost any size, shape, effective membrane surface area, or number of channels based on the above description.

Figure 4:
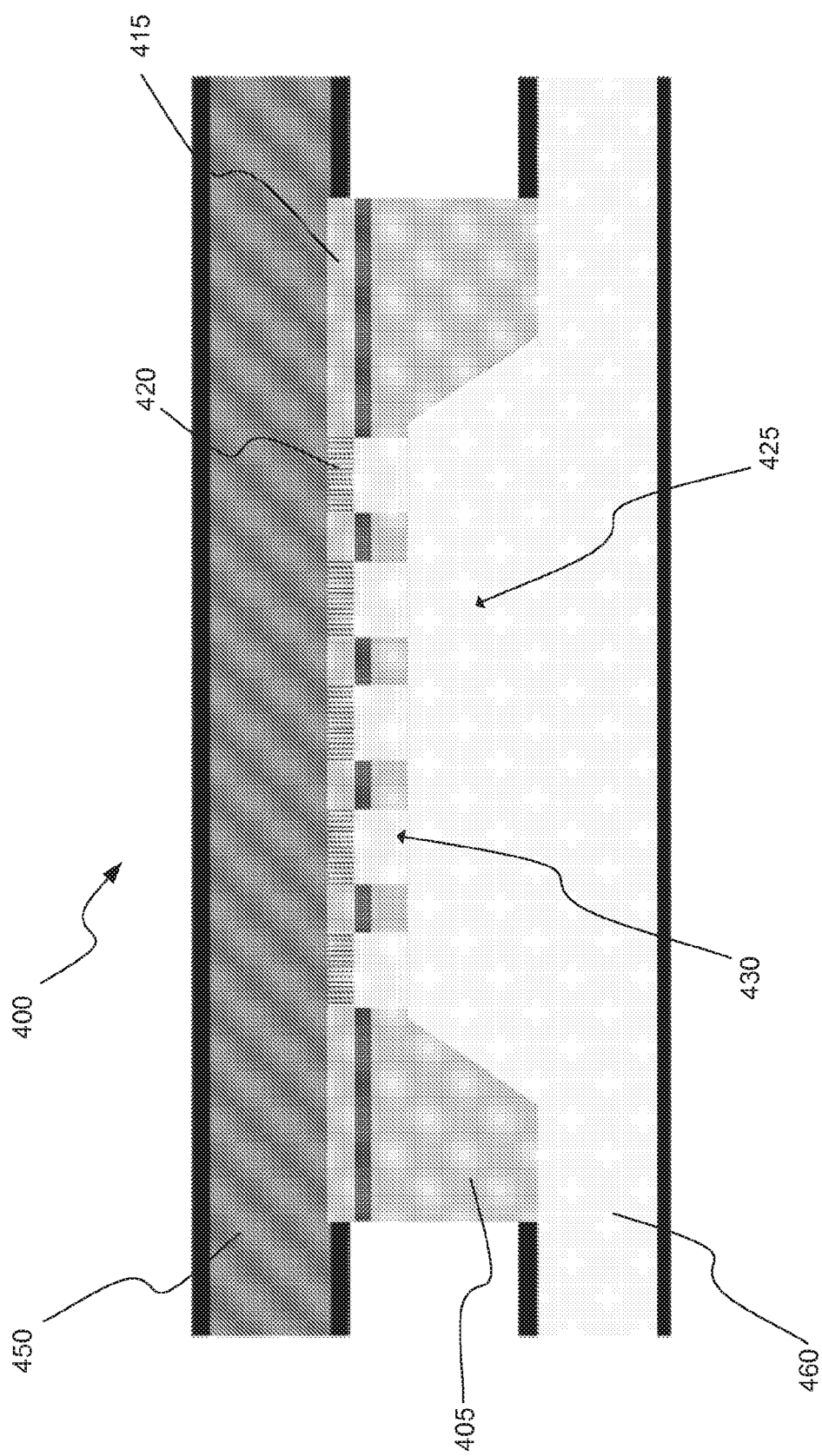
FIG. 4 shows an exemplary use of a filter according to embodiments of the present technology for allowing diffusive transport between two fluids.

FIG. 4 shows one exemplary filtration use, and displays a use of a filter according to embodiments of the present technology for allowing diffusive transport between two fluids. The filtration device 400 utilizes a filtration member formed, for example, as previously described for filtration of a fluid utilizing a second fluid. One exemplary case includes hemodialysis. In such a process, a first fluid 450, which may be blood or plasma, flows across the membrane section 415 of the filtration member. A second fluid 460, which may be dialysate, flows below the filtration member, and may flow up through the cavity 425 defined by the substrate 405. The fluids may flow in a counter current fashion, but may also flow concurrently. One or both fluids may have additional materials incorporated into the flow, such as, for example, an anticoagulant including heparin incorporated with the first fluid 450. The fluids may flow naturally or be pumped through the channels with additional pumping mechanisms (not shown). As the two fluids flow, they may be flowed with or without a pressure gradient between the fluids. For example, the hydrostatic pressure of the second fluid 460 may be reduced in order to provide ultrafiltration, or free water removal, from the first fluid 450. The filtration device 400 may be extracorporeal or be biocompatible for in vivo use. The filtration device may additionally include sensors (not shown) for determining pressure, flow, temperature, concentration of various compounds, etc. As the fluids flow across the filtration member, a concentration gradient may exist to diffuse solutes across the membrane 415 and through the pores 420 and diffusive recesses 430 in either direction. Such a concentration gradient may allow for the first fluid to release wastes, or receive nutrients from the second fluid. The second fluid 460 may flow up into the substrate 405 into the cavity 425, which may reduce the distance through which diffusion must occur, and may additionally refresh the second fluid 460 more readily in that region. After the diffusive exchange has occurred, the first fluid may be transferred back to its originating location, such as to a patient, as a filtered fluid.

Figure 5:
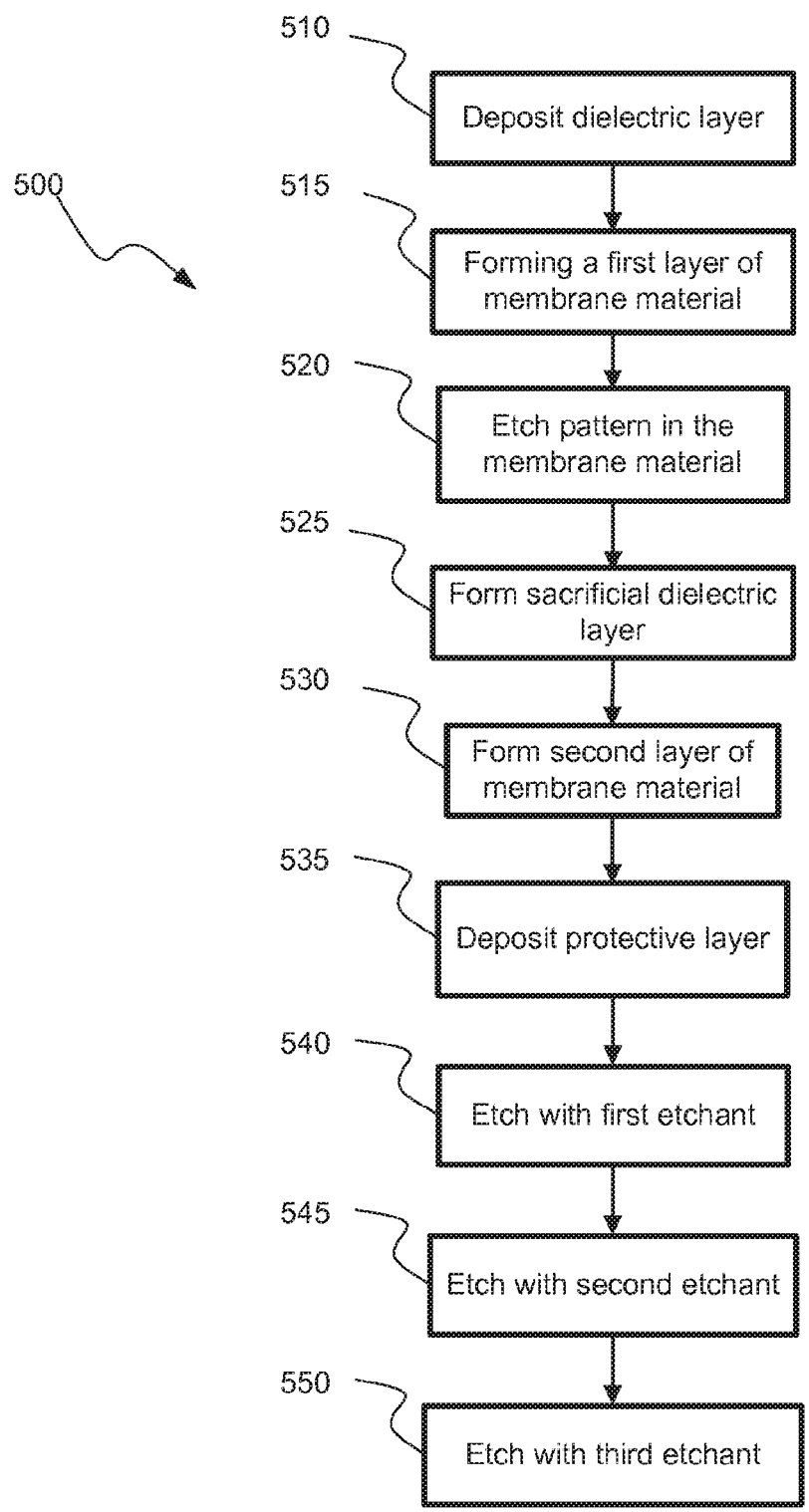
FIG. 5 shows a flow chart of a method of fabricating a filter according to embodiments of the present technology.

FIG. 5 shows a flow chart of a method 500 of fabricating a filter according to embodiments of the present technology. The method may include depositing 510 a dielectric layer over a substrate to produce an etch stop layer during thinning. The dielectric layer may be an oxide, nitride, or some other material that may protect the substrate from downward processes, and/or materials deposited over the dielectric layer from upward processes. Over the dielectric layer may be formed 515 a first membrane material layer that will become at least a part of a porous membrane. The first membrane material may be silicon based, including polysilicon, or may be some other material including metals, ceramics, and polymers chosen for qualities that may include their relative flexibility or rigidness.

The first membrane material may be etched 520 via a reactive ion etch or some other etching process that may involve a lithographic patterning process in order to form a pattern with which a pore structure may be developed. A sacrificial dielectric layer may be formed 525 over the patterned first membrane material to create the pore structures as will be later formed. The sacrificial layer may be an oxide or nitride or other material that is thermally grown over the first membrane material. The sacrificial layer may alternatively be grown by some other deposition method that can produce substantially conformal films of minimal thickness that may be, for example, about 10 nm, 7 nm, 5 nm, 3 nm, 1 nm, etc., or less. A second membrane material may be formed 530 over the first membrane material and sacrificial dielectric layer. The second membrane material may be of a similar or different material than the first membrane material, and may be, in one example, polysilicon, or some other metal, ceramic, or polymer material. The second membrane material may additionally be chosen based on particular properties or characteristics including the relative flexibility, rigidness, corrosion resistance, etc., of the material.

A protective layer may be formed 535 over the membrane materials prior to etching or further processing of the filtration device. The protective layer may be selected to be resistant to an etchant that may be used in subsequent processing steps, and may be an oxide, nitride, or some other material that may resist removal during a subsequent etching process. The filtration device may be etched 540 with a first etchant to produce one or more cavities from the backside of the substrate. In one embodiment a single cavity may be formed across the entirety of the substrate. The cavity may be formed to extend only partially through the substrate, and may not reach the level of the protective dielectric material initially deposited over the substrate. The cavity may extend through a certain percentage of the distance of the substrate that is less than about 100%, and may be less than about 99%, 98%, 97%, 96%, 95%, 94%, 93%, 92%, 91%, 90%, 85%, 80%, 75%, 70%, 65%, 60%, 55%, 50%, 45%, 40%, etc., or less. Alternatively, the protective layer may additionally be selectively patterned on the backside of the substrate in order to allow the formation of more than one cavity that are separated by the portions of the substrate remaining under the protective layer. The first etchant may be a wet or dry etchant, and in one example is a wet etchant that may be KOH or TMAH, and in another embodiment is a dry etchant comprising a reactive ion etch.

A second etching may be performed 545 to define recesses through the remaining substrate material. The second etching may be performed through the entire remaining substrate, and to the layer of the dielectric material previously formed over the substrate. The second etching may include a previous patterning to define windows through which the second etching may be performed. The windows may be of various geometries, and the resultant recesses may provide access to the membrane layers. The second etching may be a wet or dry etch, and may be a substantially anisotropic etch performed by a reactive ion etch, including a deep reactive ion etch process that extends to or past the level of the dielectric layer deposited over the substrate.

A third etching may be performed 550 to remove the protective layer and the exposed dielectric layer. The etching may also remove the sacrificial layer of material thereby exposing the pores through the membrane material layers. The third etching may be a wet or dry etching, and in one example may be a hydrofluoric acid etch. After the pores have been exposed, a plurality of apertures may exist that include at least one pore, the associated diffusive recess, and the cavity formed through the first, second, and third etching processes.

Figure 6:
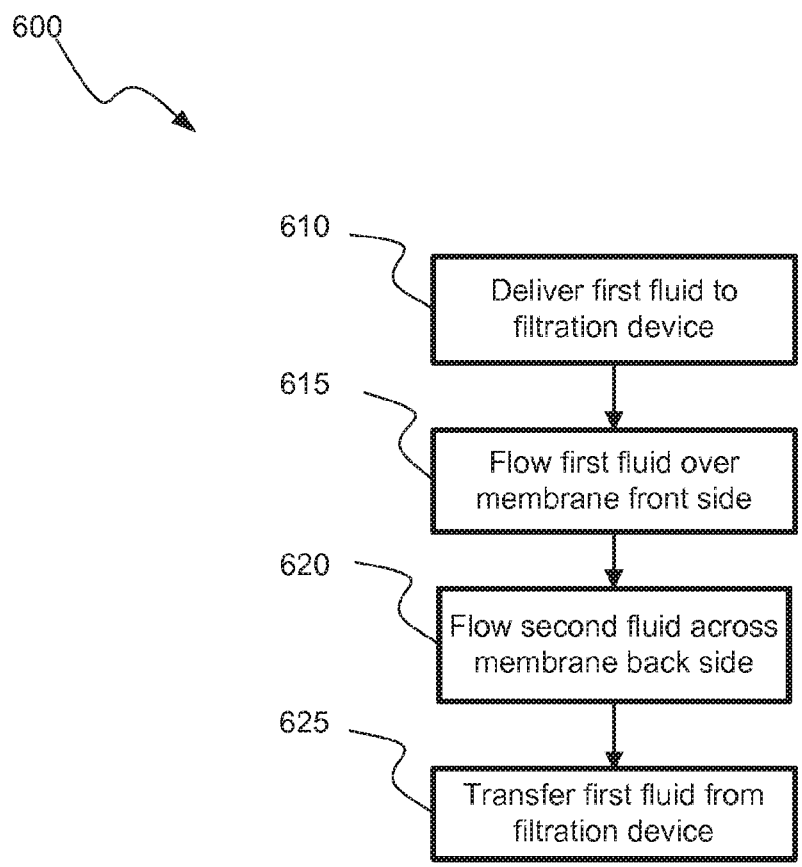
FIG. 6 shows a flow chart of a method of using a filter according to embodiments of the present technology.

FIG. 6 shows a flow chart of a method 600 of using a filter according to embodiments of the present technology. The method may include delivering 610 a first fluid to a filtration device. The filtration device may include channels for a first and second fluid, as well as a filtration member that can allow filtering of the fluids in the channels. The first fluid may be directed, flowed, or pumped 615 across a front side of the filtration member that may have a membrane with a number of pores formed therein. The pores may be of any shape and size, and may be slices or slits formed through the membrane section. A second fluid may be flowed 620 across the backside of the filtration member, and may be capable of flowing into a cavity formed in the backside of the filtration member support structure and across a plurality of recesses that provide access to the membrane section and pores. As the first and second fluid flow across the filtration member, diffusive transport may occur between the fluids in either or both directions. The transport may be based on a concentration gradient of solutes between the fluids. The fluids may have a net zero pressure gradient between them so that diffusive transport is the only available mechanism of transport. Alternatively, water may be transferred across the membrane from the first fluid to the second fluid in some embodiments due to an induced pressure gradient between the fluids. The diffusive process may result in a filtered first fluid that may be then transferred 625 from the filtration device.

An alternative embodiment for the method described by FIG. 6 is for an in vivo hemodialysis device including several membrane chips manufactured as described above. The device may also perform hemofiltration or ultrafiltration. The filtration device may be developed with a plurality of 1 cm square chips of the structures previously described. The chips may be oriented within the filtration device to create channels as described previously, so that a first fluid can be flowed between the channel formed by the front side of two chips, or across the membranes, and a second fluid can be flowed between the channel formed by the backsides of two chips, or across the membrane backside through the cavity formed in the substrates. The two fluids may be kept fluidly separate from each other by the chips such that transfer can only occur across the membranes. The formed filter may be housed in a biocompatible housing and implanted within a body. Connections may be made internally to deliver blood to the filtration device through an arterial connection and return blood to a venous connection. Alternatively, a graft, fistula, cannula, or some other connection can be used to reduce the number of internal connections. A second fluid may be delivered to the filtration device from an external source, and may be delivered to the device through the body via a port, catheter, or some other device providing access internally. Once passed through the device, the second fluid may be returned via the same port or catheter, or through a secondary port or catheter. The second fluid may be flowed through the device in a continuous loop, or may be infused for a period of time for use followed by a drainage process. Additional devices including pumps may be similarly disposed within or out from the body, and may be incorporated directly with the filtration device. Similarly sensors may be disposed within or out of the device for monitoring any number of vital statistics along with additional numbers including glucose level.

As described in FIG. 6, the first fluid, which may be blood, is delivered 610 to the filtration device through the internal connections in the body. The first fluid is flowed 615 through the device over the membrane front side. The flowing 615 may additionally include a circuit through the device that passes the first fluid through a series of channels as described previously. Alternatively, the flow is dispersed across a number of channels before being returned to a single outlet. A second fluid is flowed 620 across the backside of the membrane, and may additionally be flowed via a circuit through the device that passes the first fluid through a series of channels on the backside of the membranes. The second fluid may be dispersed across a number of channels before being returned to a single outlet in a similar fashion to the first fluid. The first and second fluids may be kept fluidly separate by the circuits such that transfer between the fluids may occur through the membranes. The first and second fluids may be pumped through the filtration device in order to maintain equal pressure across the membrane section of the filtration device. The first fluid may flow 625 or be pumped from the filtration device and return to the venous system of the body.

Figure 7:
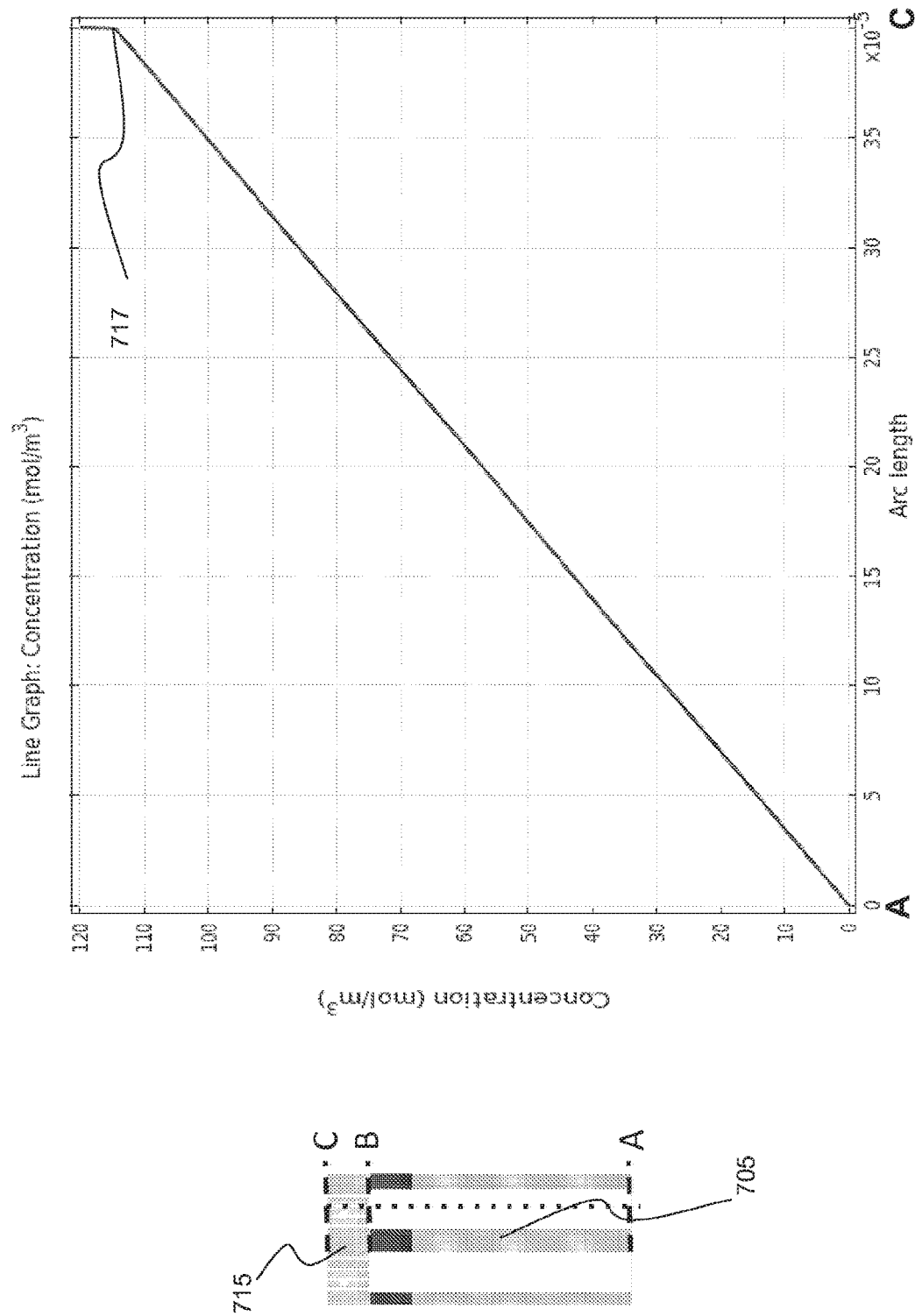
FIG. 7 shows a graph of the diffusion resistance associated with a filter structure.

FIG. 7 shows a graph of the diffusion resistance associated with a filter structure. An evaluation was performed to determine the relative resistance through an exemplary filtration device. The evaluated device included six chips having lateral dimensions of 1 cm on a side. Each chip had a 0.5 µm thick membrane over a 400 µm thick substrate. As displayed to the left of the figure, the exemplary filter structure comprises a membrane 715 over a substrate 705. As shown, a distance is represented as A to B for the distance from the bottom of the substrate to the bottom of the membrane structure. A distance is also represented as B to C for the distance from the bottom of the membrane structure to the top of the membrane structure. Hence, a distance A to C shows the distance through which diffusion may progress for an exemplary filtration device. The associated chart shows the concentration gradient from point A, as depicted by the left end of the X-axis, to point C, as depicted by the right end of the X-axis. The inflection point 717 represents point B, or the interface between the membrane and the substrate. As can be seen, only 5% of the concentration gradient occurs between points B and C, or across the membrane. 95% of the concentration gradient, and accordingly 95% of the transport resistance occurs through the substrate. The species diffusion resistance through a channel can be modeled as a function of the length of the channel divided by the product of the diffusion coefficient for the species and the cross-sectional area for the channel. Hence, as the length increases, or the area decreases, the resistance increases proportionately. Accordingly, by reducing the length of the diffusive channel, a proportionate decrease in the diffusive resistance can be expected. Put another way, if the same level of resistance can be tolerated by the system, by reducing the length for diffusive transport, a reduced area may be utilized to provide the same degree of function.

Figure 8:
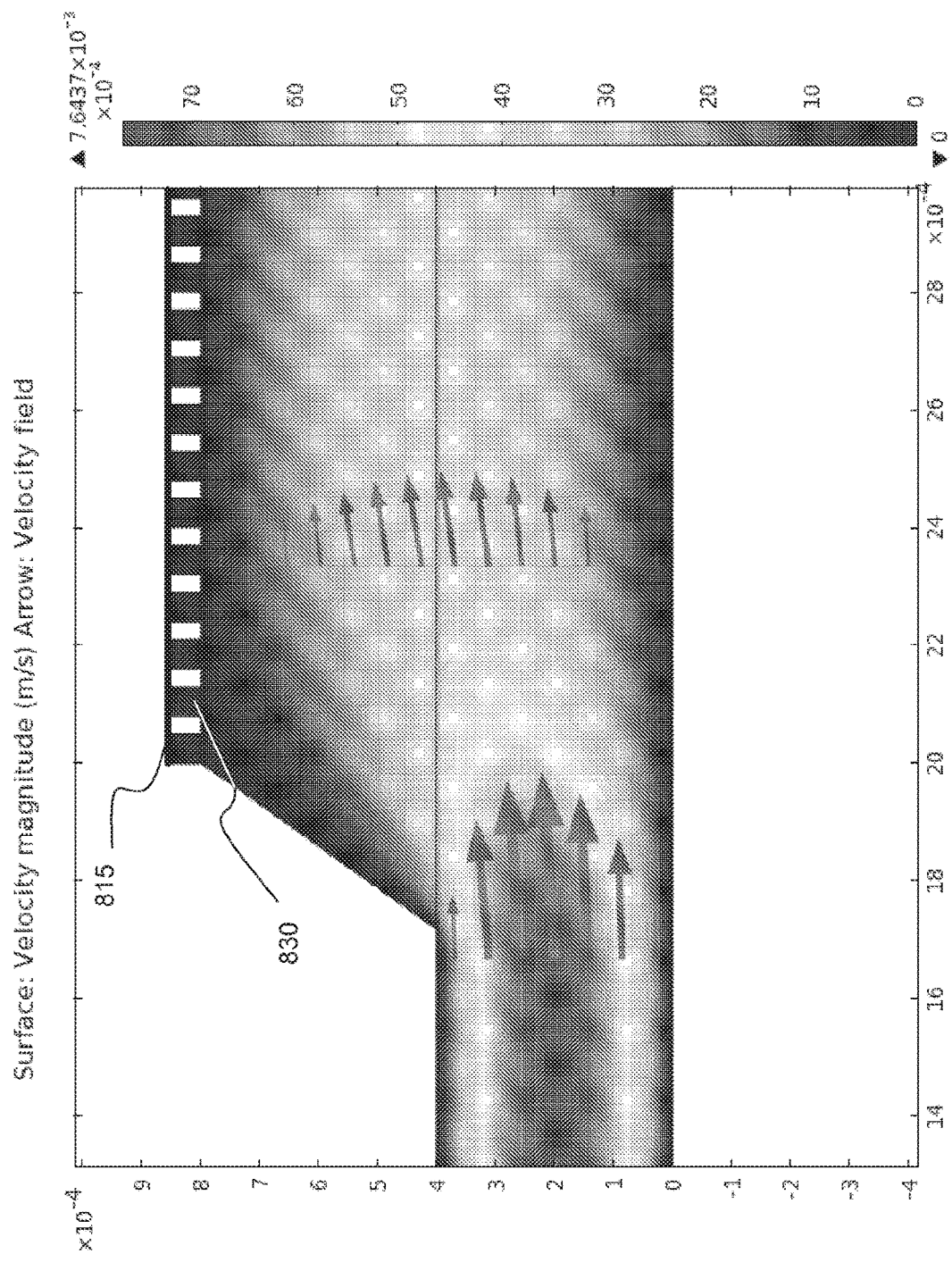
FIG. 8 shows a graph of the modeled flow of a fluid along the backside of a filter fabricated according to embodiments of the present technology.

FIG. 8 shows a graph of the modeled flow of a fluid along the backside of a filter fabricated according to embodiments of the present technology. The fluid flows into a cavity formed in the backside of a filtration device, and delivers the fluid to diffusive recesses 830. The diffusive recesses 830 along with porous membrane 815 allow diffusive transport between the fluid and an additional fluid that may be flowed across the top side of the membrane 815. By providing a cavity through which the fluid may be delivered, the refresh rate of fluid transfer may be improved near the diffusive recesses 830. Additionally, the diffusive transport may be improved due to the reduced distance through which diffusion occurs, which may provide a concomitant reduction in the system transport resistance.

Figure 9A:
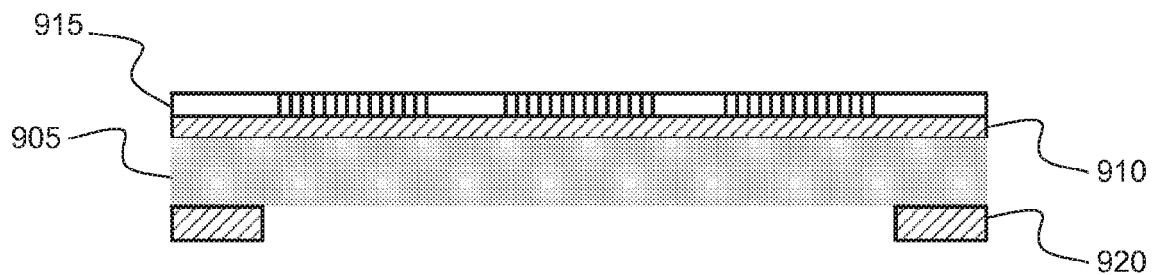
FIGS. 9A-9C show cross-sectional views of a filter during certain steps of a method for making a filter according to embodiments of the present technology.
Figure 9B:
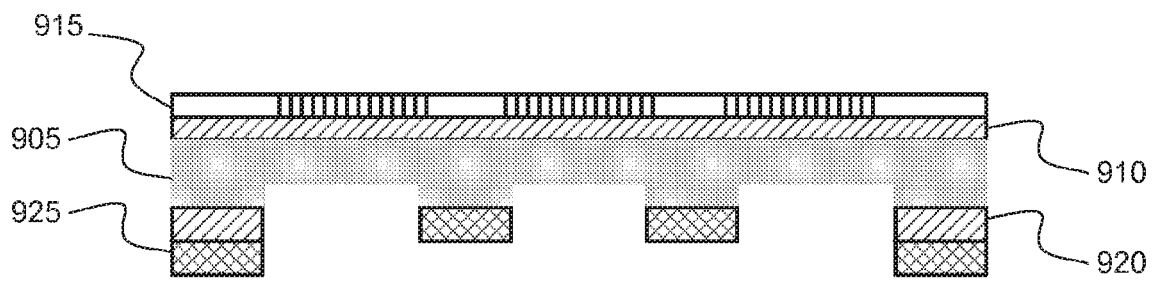
Figure 9C:
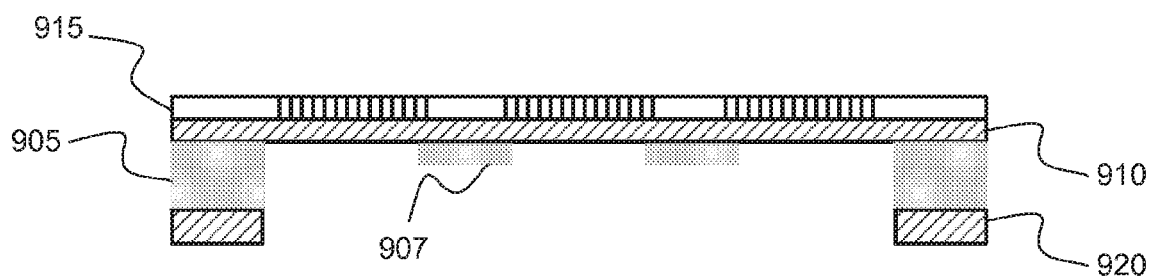

Turning to FIG. 9, cross-sectional views of exemplary filter structures are shown according to embodiments of the present technology. The figures illustrate an additional process for performing the backside etching of the filter structures. Some or all of the steps as previously described with respect to other structures may be incorporated into the processes as illustrated. FIG. 9A shows a portion of a filter structure after front side processing has been performed. Substrate 905 may include overlying protective oxide 910, as well as polymeric material 915 including the defined pores. The materials may include any of the materials as previously described with respect to other structures. Additionally, the pores in polymeric material 915 may include any of the structures or dimensions as previously described. After front side processing has been completed, the backside protective layer 920 may be formed and patterned as illustrated. Protective layer 920 may include any of the materials as previously described and may include an oxide layer similar to or different from layer 910. The patterning of backside layer 920 may be performed to define the recess areas through which access to the filter membranes may be achieved as previously described, and may specifically define the cavity structures to be formed prior to or during the formation of the recess areas. The recesses may be of any of the dimensions or geometries as previously described, and may be, for example, about 10 mm×10 mm or less, and maybe for example 8 mm×8 mm, 6 mm×6 mm, 4 mm×4 mm, 2 mm×2 mm, etc. or less.

After backside layer 920 has been patterned, an additional layer of material 925 may be formed over the backside structures. Material 925 may be any of the previously described materials, and may be, for example, a resist layer. Material layer 925 may be formed over and within the cavity areas defined by the patterning of backside layer 920, in order to define the recess or window layers for the final filters. Depending on the desired dimensioning of the windows, the positioning of the material layer 925 may be adjusted accordingly. The defined windows may be of any of the dimensions as previously described, and may be of a variety of geometries as may be useful in the final filters. For example, the windows may be defined as rectangles having a first dimension longer than a second dimension. Either or both of the first dimension and second dimension may be greater than or less than about 500 µm in disclosed embodiments. Alternatively, either or both of the first dimension and second dimension may be less than or equal to about 400 µm, 300 µm, 250 µm, 200 µm, 150 µm, 100 µm, 50 µm, 25 µm, 15 µm, 10 µm, 5 µM, etc. or less. For example, the first dimension may be less than or about 300 µm, and the second dimension may be less than or about 100 µm.

As illustrated in FIG. 9B, resist 925 may be deposited over the patterned oxide layer 920, as well as within the defined recess regions. An etching process may be performed in order to etch through the backside of substrate layer 905. The etching may be performed via any of the processes as previously described, and may be for example, a DRIE etch. The DRIE etch may be performed to a depth in order to define the length of the final support structure required between window sections. For example, the deeper the initial etch performed, the thicker the support structure remaining. The etch may be performed to a depth greater than or less than about 5 µm, and may be performed greater than or about 10 µm, 20 µm, 30 µm, 40 µm, 50 µm, 60 µm, 75 µm, 90 µm, 100 µm, 125 µm, 150 µm, 200 µm, etc. or more. After the required etch depth has been reached, the etch process may be stopped and material layer 925 may be stripped. The exposed substrate 905 may include a stepped structure within the recess regions due to the material layer 925 preventing regions of the substrate 905 from being exposed to the etch process. A second etch process may be performed that is similar to or different from the previous etch process. For example, a second DRIE etch may be performed down to the layer of oxide 910. Because the etch process may be uniform across the surface of the substrate 905, the stepped structure may be maintained to the level of oxide layer 910. Accordingly, the steps originally protected by material layer 905 may be the only remaining material upon the completion of the etch process. Final finishing may then be performed to remove the exposed regions of oxide layer 910, which may then expose the filter regions that may be further protected and supported by the remaining substrate sections 907.

Figure 10A:
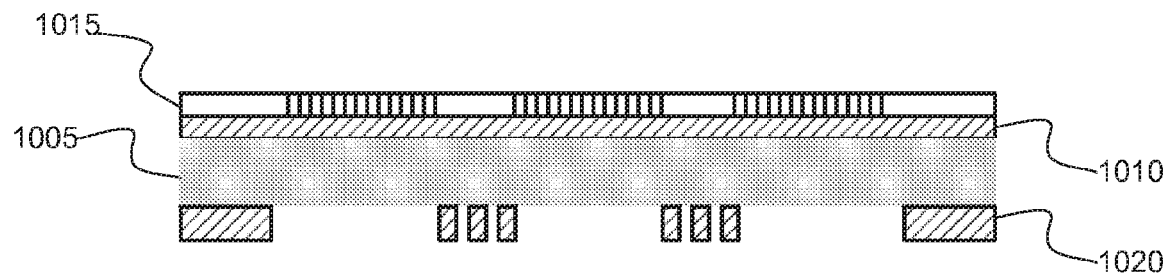
FIGS. 10A-10C show cross-sectional views of a filter during certain steps of a method for making a filter according to embodiments of the present technology.
Figure 10B:
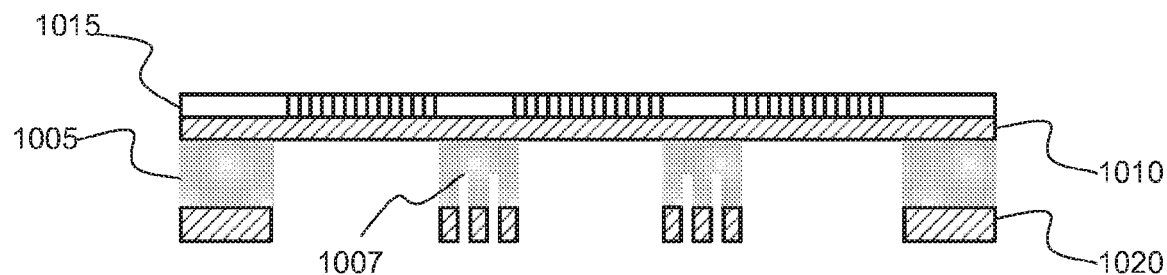

Turning to FIG. 10, cross-sectional views of exemplary filter structures are shown according to embodiments of the present technology. The figures illustrate an additional process for performing the backside etching of the filter structures. Some or all of the steps as previously described with respect to other structures may be incorporated into the processes as illustrated. Substrate 1005 may include overlying protective oxide 1010, as well as polymeric material 1015 including the defined pores. The materials may include any of the materials as previously described with respect to other structures. Additionally, the pores in polymeric material 1015 may include any of the structures or dimensions as previously described. After front side processing has been completed, the backside protective layer 1020 may be formed and patterned as illustrated. Protective layer 1020 may include any of the materials as previously described and may include an oxide layer similar to or different from layer 1010. Protective layer 1020 may be patterned to include both large and small openings as illustrated in FIG. 10A. The small openings may include spacing between each section of material 1020 of from less than or about 1 µm to about 100 µm or more in disclosed embodiments. The spacing may be less than, greater than, or about 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, etc. or more.

Figure 10C:
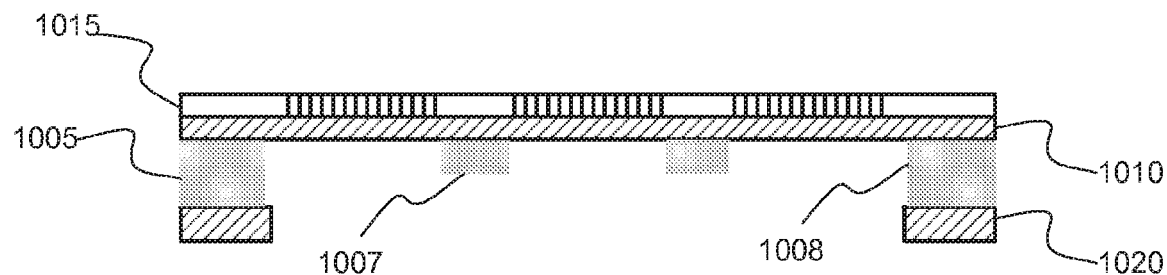

An etching process may be performed to remove the exposed regions of substrate 1005. Oxide layer 1010 may be used as an etch stop for the etching process. Any of the previously described etching processes may be performed, and a DRIE etch may be performed as previously described. The patterning of protective layer 1020 forming both large and small openings may be used to take advantage of a natural phenomenon known as aspect-ratio-dependent-etch rate, or ARDE. This phenomenon may cause smaller area recesses to etch more slowly than larger regions. Accordingly, when larger regions have been etched down to layer 1010, areas between the smaller openings in layer 1020, such as region 1007, may not be etched down to the layer of oxide layer 1010. The DRIE etch may be an anisotropic etch, and may not suffer from edge creep into the regions under protective layer 1020. A subsequent isotropic etch may be performed to undercut the remaining pillar structures around region 1007, leaving support regions 1007 between the exposed filter sections. The isotropic etch may be any wet or dry etch as previously discussed, and may be, for example, an $SF_6$ preparation. The isotropic etch may additionally undercut support pillars 1008, as illustrated in FIG. 10C. Accordingly, in order to ensure adequate support structure around the cavities for each chip, this undercut may be compensated for in the initial masking process. A benefit of such a process is that only one backside mask may be needed, which may reduce queue times.

Figure 11A:
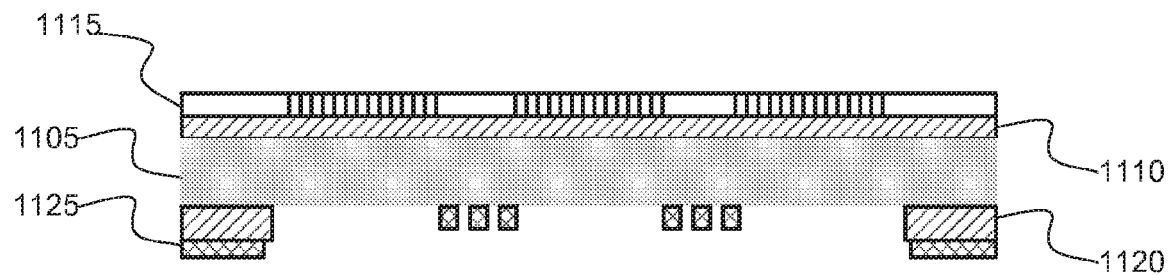
FIGS. 11A-11C show cross-sectional views of a filter during certain steps of a method for making a filter according to embodiments of the present technology.
Figure 11B:
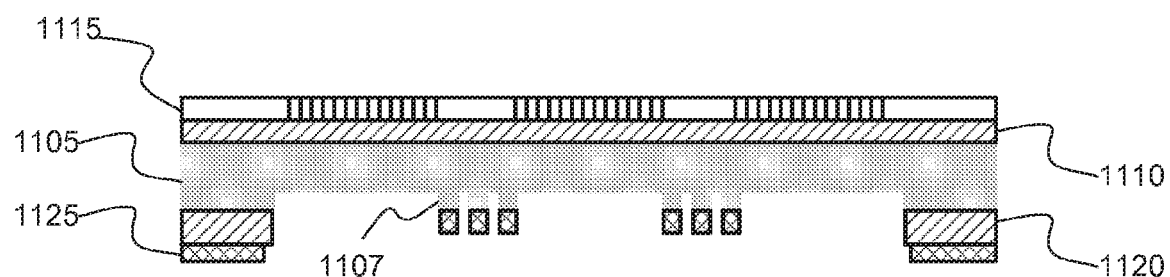

Turning to FIG. 11, cross-sectional views of exemplary filter structures are shown according to embodiments of the present technology. The figures illustrate an additional process for performing the backside etching of the filter structures. Some or all of the steps as previously described with respect to other structures may be incorporated into the processes as illustrated. Substrate 1105 may include overlying protective oxide 1110, as well as polymeric material 1115 including the defined pores. The materials may include any of the materials as previously described with respect to other structures. Additionally, the pores in polymeric material 1115 may include any of the structures or dimensions as previously described. After front side processing has been completed, the backside protective layer 1120 may be formed and patterned as illustrated. Protective layer 1120 may include any of the materials as previously described and may include an oxide layer similar to or different from layer 1110. Protective layer 1120 may be patterned to include both large and small openings as illustrated in FIG. 11A, which may include any of the dimensions as previously discussed. Protective layer 1120 may be formed to compensate for expected removal that may occur during the process. Layer 1120 may be, for example, a low temperature oxide formed to a thickness greater than or about 1 µm, and may be greater than or about 2 µm, 5 µm, 7 µm, 10 µm, etc. or more. This material may have a known selectivity with respect to the substrate 1105, such as a silicon substrate, based on the etch process being performed. For example, a low temperature oxide may have a selectivity compared to silicon of about 100:1 for a certain etch process, such as a DRIE etch process.

An additional layer 1125 may be formed over the patterned protective layer 1120 as well as within the exposed recess regions. Larger and smaller areas between portions of material 1125 may be formed as illustrated, for example. Layer 1125 may be any of the previously described layers, and may be, for example, a resist layer. An initial etch may be performed down to a first depth, which may be based on a desired thickness for the final support structures. The first etch may be a substantially anisotropic etch and may be, for example, a DRIE etch. The first etch may be performed to a first depth through substrate 1105, and the first depth may be greater than or about 1 µm and may be greater than or about 2 µm, 5 µm, 10 µm, 15 µm, 20 µm, 25 µm, 30 µm, 50 µm, etc. or more in disclosed embodiments. After the first depth has been reached, the etching process may be stopped, and resist layer 1125 may be stripped from the substrate and overlying protective layer 1120. The etching process may then be resumed down to the level of protective layer 1110, which may again act as an etch stop for the etching process. As explained previously with respect to other described processes, the stepped structure formed across the exposed recess regions of substrate 1105 may be maintained throughout the etching process down to the level of layer 1110. Depending on the etching process performed, the etch may additionally affect protective layer 1120, however based on the selectivity to the oxide as compared to silicon, for example, as well as the initial amount of protective layer 1120 deposited, protective layer 1120 may not be completely removed during the processing in order to protect or maintain the cavity structure. As with the previous approach, this process may reduce the number and types of etchings that may be performed, and may similarly reduce overall queue times during device fabrication.

Figure 11C:
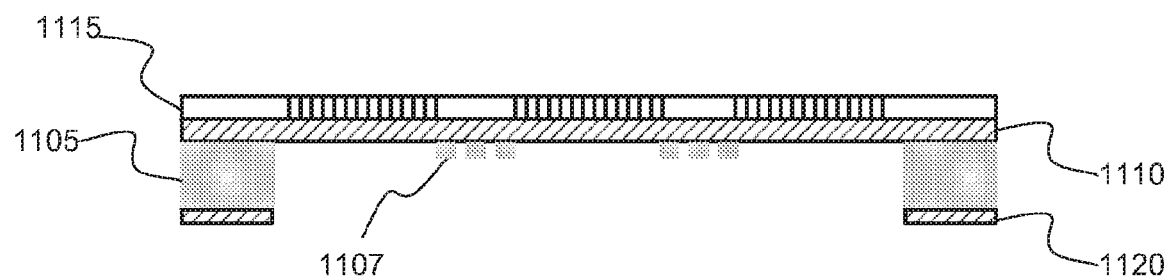

In an alternative embodiment, resist layer 1125 may be formed and patterned with large and small divider areas prior to, or in lieu of, the formation of protective layer 1120. An initial etch may be performed over the resist layer 1125 as previously described down to a first depth within the substrate 1105. Etch layer 1125 may then be stripped. An additional resist layer may be formed over the support structures between recess regions while leaving the stepped structure previously formed within the recess regions exposed. In disclosed embodiments, the additional resist may not fully cover the support structures in order to allow for over-exposure of a subsequent etching process. The subsequent etch may then be capable of removing pooled resist that may remain within the formed cavities in the stepped structure of the substrate 1105, for example. For example, UV exposure may be used to remove unwanted resist remaining within the stepped structure. As illustrated in FIG. 11C, an etching process such as a DRIE etch may then be performed in order to remove the exposed stepped structure of the substrate 1105 down to the level of protective layer 1110. Any remaining resist may then be stripped from the final filter structure before finishing processes are performed. Such a process may be advantageous because an additional oxide layer may not be needed. Because such a layer may require additional or substantial time to form, removing such a layer from the process may further improve queue times.

Turning to FIG. 12, cross-sectional views of exemplary filter structures are shown according to embodiments of the present technology. The figures illustrate an additional process for performing the backside etching of the filter structures. Some or all of the steps as previously described with respect to other structures may be incorporated into the processes as illustrated. Substrate 1205 may include overlying protective oxide 1210, as well as polymeric material 1215 including the defined pores. The materials may include any of the materials as previously described with respect to other structures. Additionally, the pores in polymeric material 1215 may include any of the structures or dimensions as previously described. After front side processing has been completed, the backside protective layer 1220 may be formed and patterned as illustrated. Protective layer 1220 may include any of the materials as previously described and may include an oxide layer similar to or different from layer 1210. Protective layer 1220 may be patterned to provide a plurality of access regions through substrate 1205, which may have any of the dimensions as previously listed. Protective layer 1220 may be of a variety of thicknesses as previously described, and may be greater than or about 10 Å in disclosed embodiments, and may additionally be greater than or about 25 Å, 50 Å, 75 Å, 1 µm, 2 µm, 5 µm, etc. or more. A resist layer 1225, or additional protective layer, may be formed over the edge supports in order to protect these regions from subsequent etching processes. The resist layer 1225 may be of a similar dimension to the corresponding portion of protective layer 1220 over which it lies, and may be slightly smaller, for example, in order to allow for removal of edge regions of the exposed recesses.

Figure 12A:
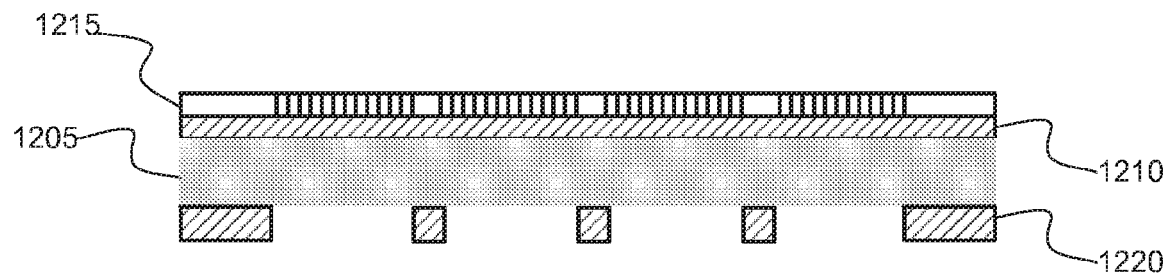
FIGS. 12A-12C show cross-sectional views of a filter during certain steps of a method for making a filter according to embodiments of the present technology.
Figure 12B:
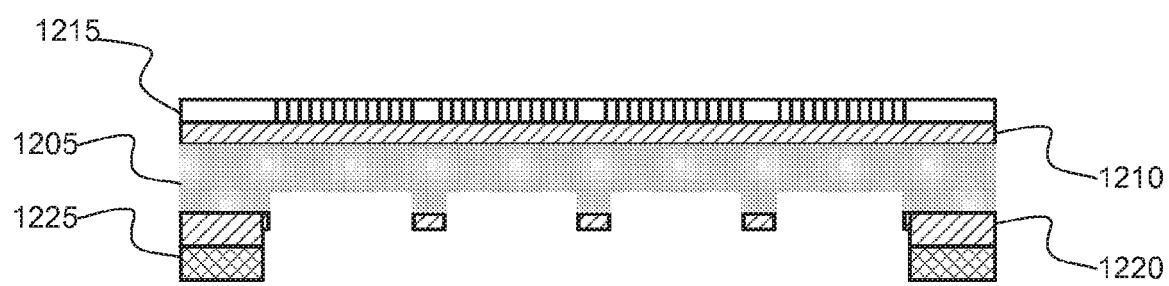
Figure 12C:
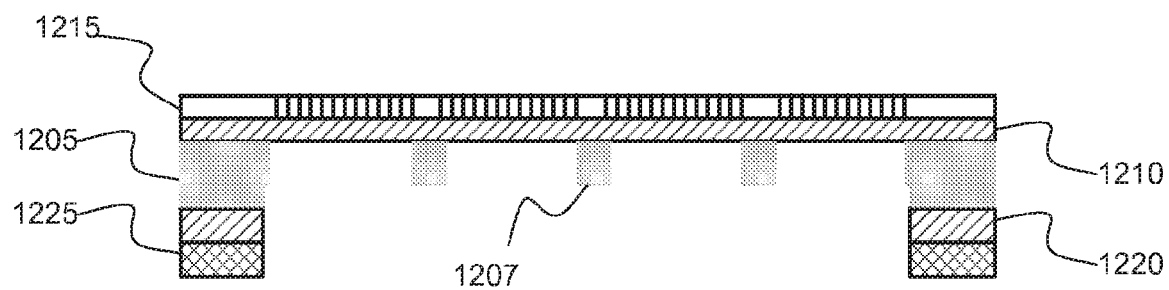
Figure 12D:
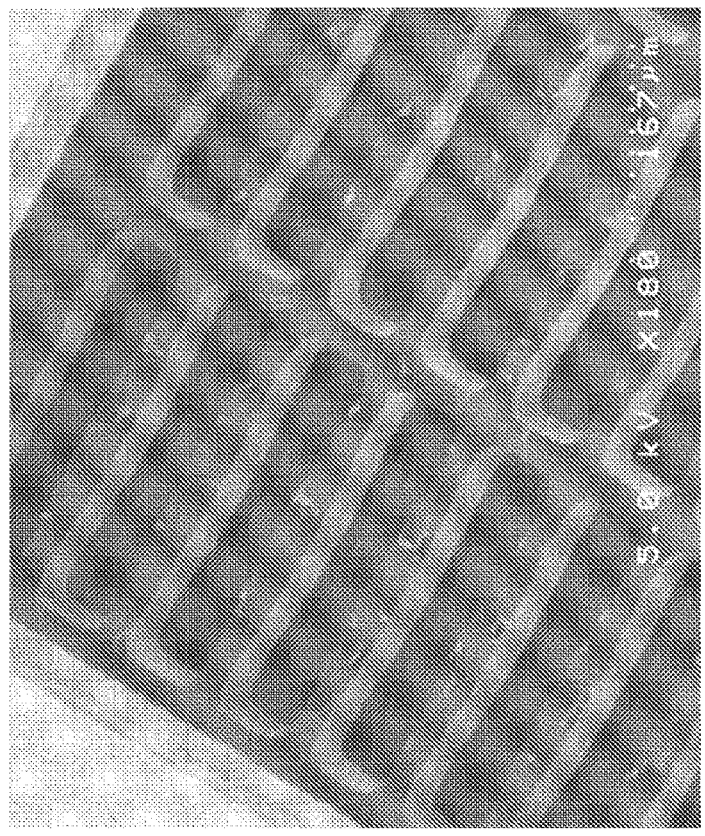
FIG. 12D shows SEM images of exemplary structures produced according to embodiments of the present technology.
Figure 12D:
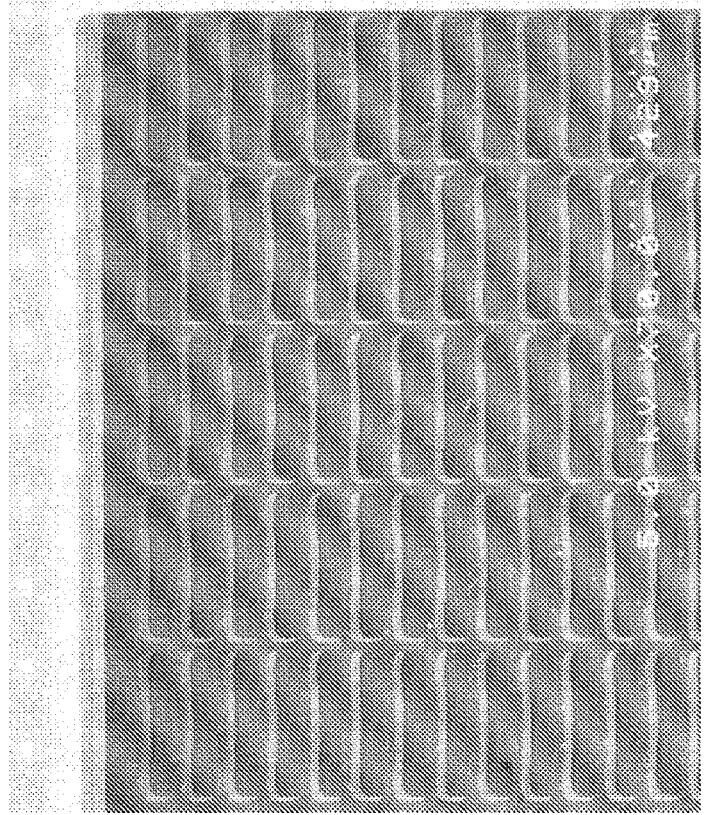

An etch process such as previously described, for example, may be performed over the exposed structures. As illustrated in FIG. 12B, an etch process may be performed that etches both protective layer 1220 as well as substrate 1205, although at different rates. For example, protective layer 1220 may be an oxide layer that etches slower than the material of substrate 1205, such as silicon, for example. The protective layer 1220 material, the thickness of the layer, as well as the etch process performed may all be adjusted in order to produce the desired structure. For example, protective layer 1220 may be formed of a material that has a known selectivity for a particular etch process as compared to silicon. For example, the selected material may have a selectivity of greater than or about 50:1 as compared to silicon, or may be greater than or about 75:1, 100:1, 120:1, 150:1, etc. or more. The higher the selectivity, the slower the material will etch as compared to silicon, and the thicker remaining portions 1207 will be. The portions of protective layer 1220 covering support sections 1207 may or may not be completely etched during the process, which may or may not allow etching of underlying regions 1207. As illustrated in FIG. 12D, such a process may provide fairly uniform structures across a substrate and may compensate for intra-wafer non-uniformity by adjusting the oxide thickness at different areas on the wafer. For example, oxide layer 1220 may be formed thicker towards the edge regions of the areas to be removed. Additionally, the process may not require deep-pit lithography or re-patterning once the etch process is started, and therefore such a fabrication process may be performed with a single etch down to the layer of the filter membranes or underlying protective oxide layer 1210. Additionally, by utilizing a material with a higher selectivity ratio as compared to silicon, less of the material may need to be deposited for the process, which may further reduce queue times.

Turning to FIG. 13, cross-sectional views of exemplary filter structures are shown according to embodiments of the present technology. The figures illustrate an additional process for performing the manufacturing of the filter structures. As will be understood, the figures disclosed may illustrate only a portion of a larger filter structure, such as illustrated in FIG. 2, for example. Some or all of the steps as previously described with respect to other structures may be incorporated into the processes as illustrated. Protective layer 1320, such as an oxide, may be formed and patterned over a substrate 1305 in order to produce a stepped structure such as illustrated in FIG. 13A. This protective layer 1320 may be formed over what will become the backside of substrate 1305. The substrate 1305 may then be flipped and bonded to a subsequent wafer. Substrate 1305 may then be planarized to a desired thickness of the final filter supports, and front side processing may be performed as previously described, which may include forming protective layer 1310 and filter layer 1315 as illustrated. Planarizing substrate 1305 may reduce the thickness of the substrate 1305 below about 1 mm, and may reduce the thickness of the substrate to below or about 750 µm, 500 µm, 250 µm, 100 µm, 75 µm, 50 µm, 25 µm, 15 µm, 10 µm, 5 µm, etc. or less.

Figure 13A:
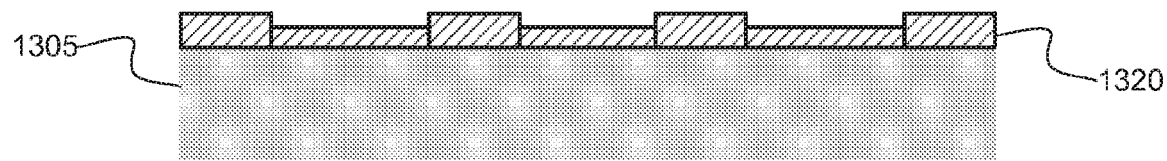
FIGS. 13A-13D show cross-sectional views of a filter during certain steps of a method for making a filter according to embodiments of the present technology.
Figure 13B:
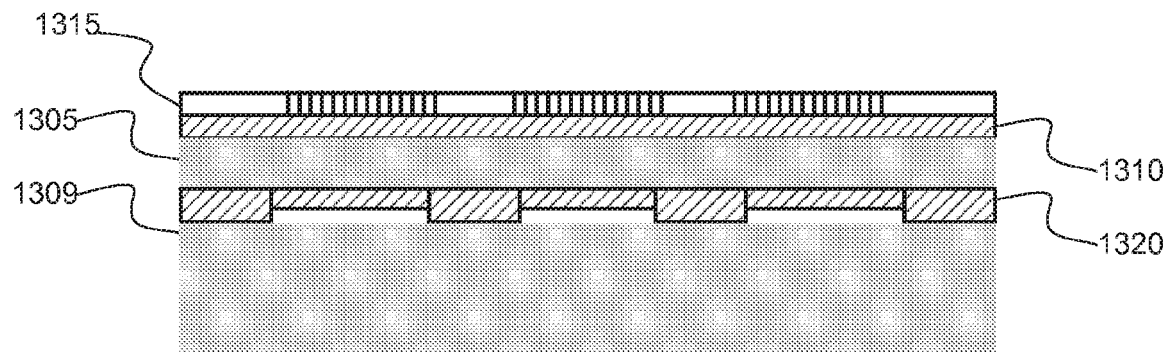
Figure 13C:
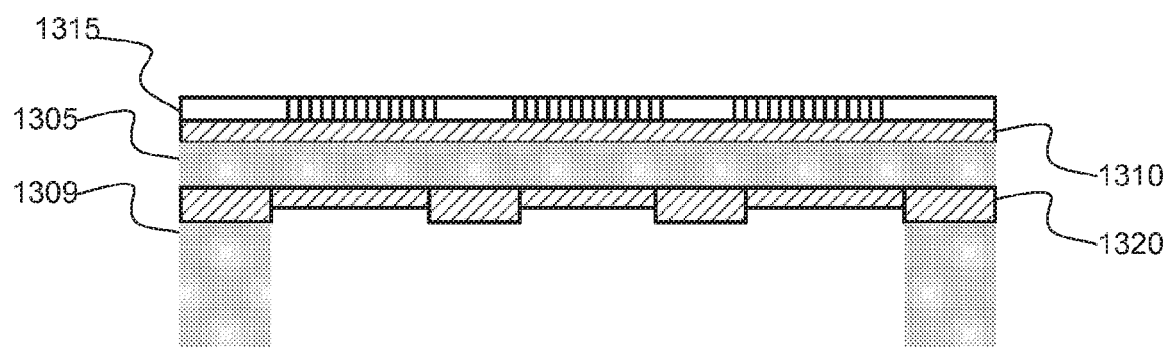
Figure 13D:
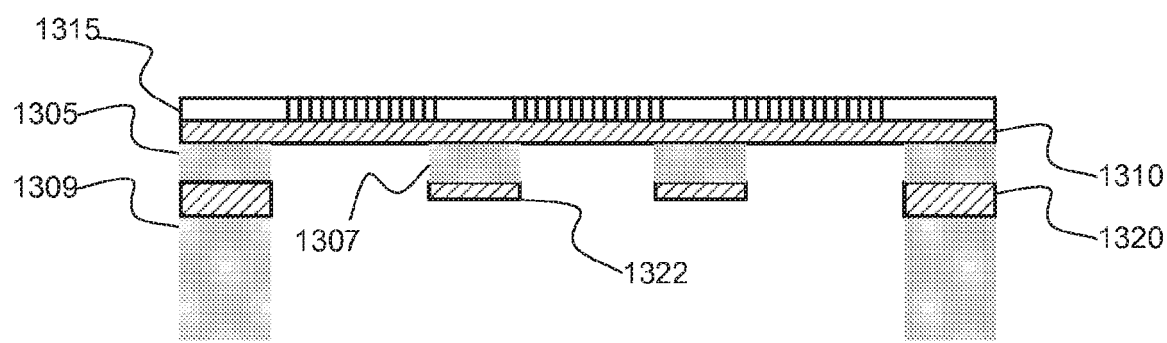
Figure 14A:
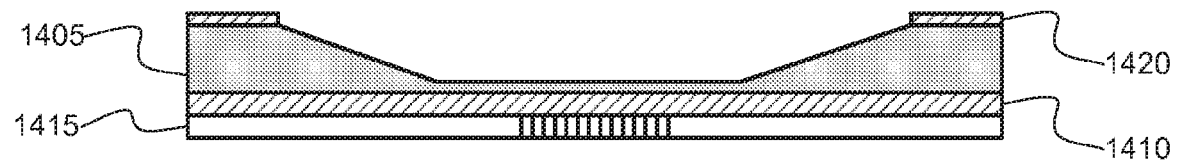
FIGS. 14A-14D show cross-sectional views of a filter during certain steps of a method for making a filter according to embodiments of the present technology.
Figure 14B:
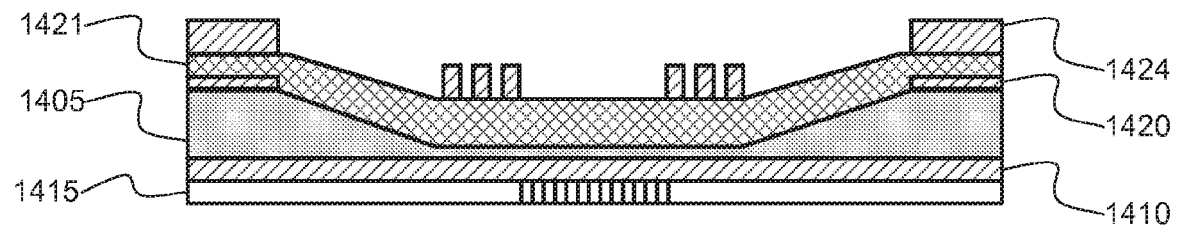
Figure 14C:
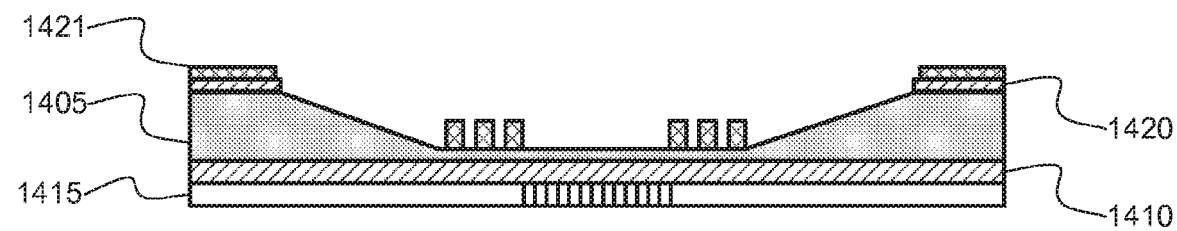
Figure 14D:
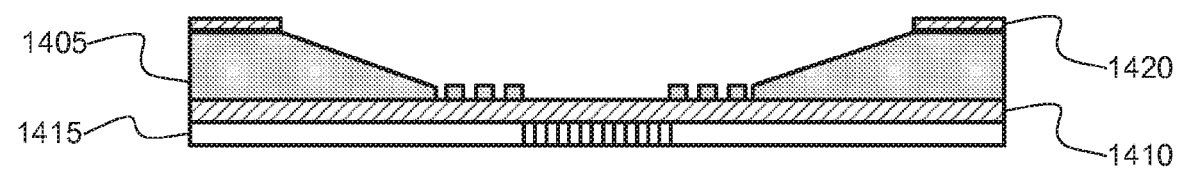
Figure 15A:
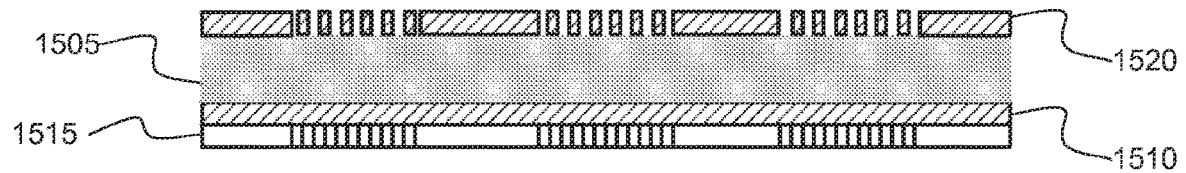
FIGS. 15A-15D show cross-sectional views of a filter during certain steps of a method for making a filter according to embodiments of the present technology.
Figure 15B:
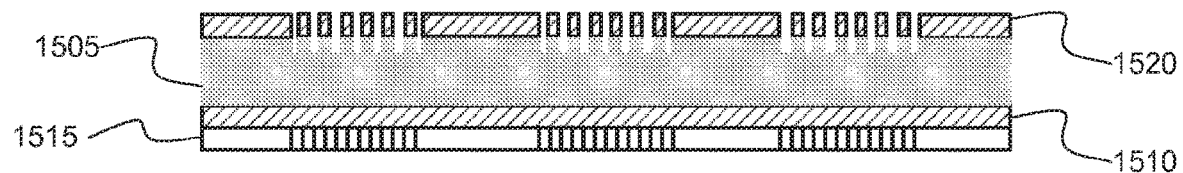
Figure 15C:
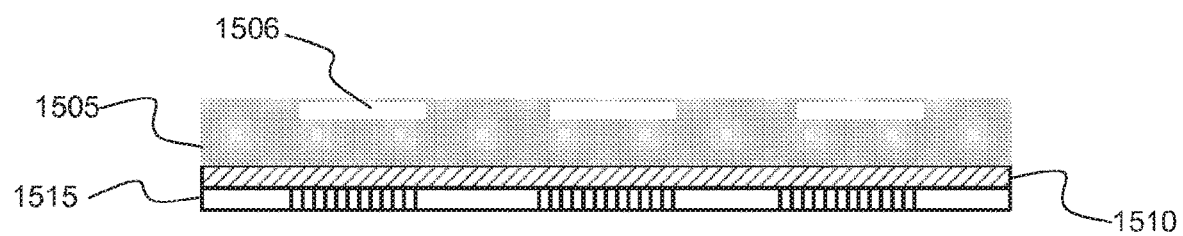
Figure 15D:
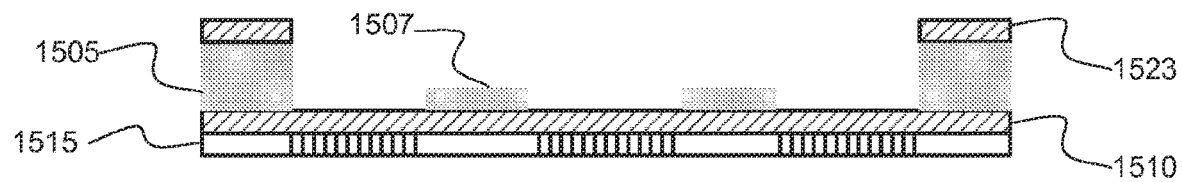

As illustrated in FIG. 13C, an etch may be performed through the bonded wafer to expose the stepped layer 1320. A subsequent etch or the same etch through the bonded wafer may be performed through the protective layer 1320 and substrate 1305 down to the level of protective layer 1310. The stepped structure of layer 1320 may allow supports 1307 to be maintained based on similar selectivity principles as previously described, due to the thicker portions of layer 1320 overlying those regions. As illustrated in FIG. 13D, the thicker portions of layer 1320 may or may not be completely etched during the process, and may maintain a portion of layer 1320 such as illustrated with sections 1322.

Turning to FIG. 14, cross-sectional views of exemplary filter structures are shown according to embodiments of the present technology. The figures illustrate an additional process for performing the backside etching of the filter structures. Some or all of the steps as previously described with respect to other structures may be incorporated into the processes as illustrated. Substrate 1405 may include overlying protective oxide 1410, as well as polymeric material 1415 including the defined pores. The materials may include any of the materials as previously described with respect to other structures. Additionally, the pores in polymeric material 1415 may include any of the structures or dimensions as previously described. After front side processing has been completed, the backside protective layer 1420 may be formed over the support structure regions of substrate 1405. An etch producing sloped walls within substrate 1405 may be performed, such as the KOH etch as previously described almost down to the protective layer 1410, such as within about 10 µm, 5 µm, 1 µm, 800 nm, 600 nm, 500 nm, 400 nm, 300 nm, 250 nm, 200 nm, 150 nm, 100 nm, 50 nm, etc., or less. A resist layer 1421 may be formed over the substrate structure, and as illustrated in FIG. 14B, may pool within the formed recess in the substrate 1405. A lithography process utilizing UV exposure may be performed with contact mask features 1424. Such a process may remove the exposed resist, while maintaining the portions residing under the defined contact mask regions. A subsequent etch may be performed through a portion of the exposed substrate 1405 prior to stripping remaining resist material 1421 down to the layer of protective layer 1410. Such a process may provide more uniform intra-wafer depth control based on the wet etch performed initially. Additionally, performing a wet etching process, such as described throughout the specification may allow for batch processing of many wafers at a time, which may further reduce queue times.

Turning to FIG. 15, cross-sectional views of exemplary filter structures are shown according to embodiments of the present technology. The figures illustrate an additional process for performing the backside etching of the filter structures. Some or all of the steps as previously described with respect to other structures may be incorporated into the processes as illustrated. Substrate 1505 may include overlying protective oxide 1510, as well as polymeric material 1515 including the defined pores. The materials may include any of the materials as previously described with respect to other structures. Additionally, the pores in polymeric material 1515 may include any of the structures or dimensions as previously described. After front side processing has been completed, the backside protective layer 1520 may be formed and patterned as illustrated. Protective layer 1520 may include any of the materials as previously described and may include an oxide layer similar to or different from layer 1510. Protective layer 1520 may be patterned to provide a plurality of gaps exposing regions of substrate 1505. An etching process may be performed down to a first depth through the substrate 1505. The first depth may be based on the desired final thickness of support structures that may be maintained between filter areas. For example, the first depth may be greater than or about 5 µM, and may be greater than or about 10 µm, 15 µm, 20 µm, 30 µm, 40 µm, 50 µm, 60 µm, 75 µm, 100 µm, 150 µm, etc. or more. Such a process may produce a series of shallow trenches within the substrate 1505.

Figure 16:
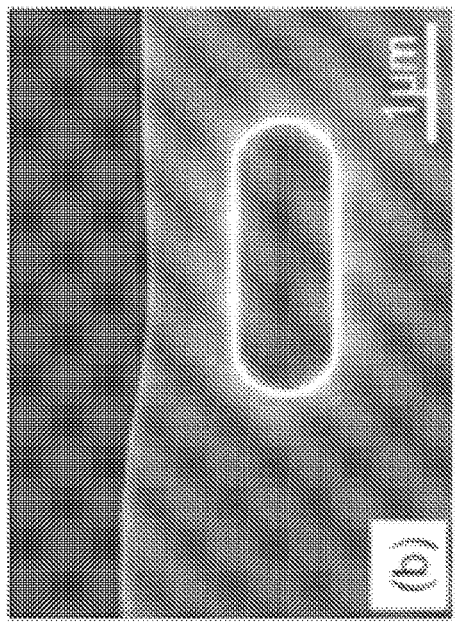
FIG. 16 shows SEM images of exemplary structures produced according to embodiments of the present technology.
Figure 16:
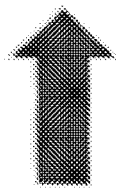
Figure 16:
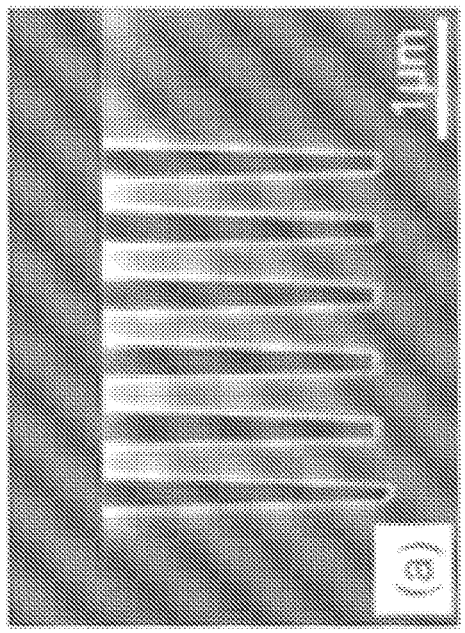

The backside protective layer 1520 may be removed from the substrate 1505, and an anneal or subsequent process may be performed to merge the series of shallow trenches into one or more cavities 1506 within the surface of the substrate 1505. Depending on the number and patterning of the shallow trenches, cavities 1506 may form voids, pipes, plates, or other geometries within the substrate 1505. An additional material layer 1523, such an oxide or resist, for example, may be deposited and patterned over the regions of the substrate 1505 corresponding to support structures between final filter sections, such as the cavities as previously described. An etch process may then be performed through the exposed substrate. Because of the cavities 1506 within the substrate structure, regions of the substrate 1505 in line with the cavities 1506 may etch at a faster rate than regions of the substrate 1505 still intact. The etch process may be performed down to the level of protective layer 1510, and based on the cavities 1506 locations, support structures 1507 may be maintained between the window areas that may expose the filter regions. Turning to FIG. 16, SEM images are shown of an annealing process used to convert a series of narrow trenches within a substrate into a void under the substrate surface as described above.

In the preceding description, for the purposes of explanation, numerous details have been set forth in order to provide an understanding of various embodiments of the present technology. Having disclosed several embodiments, it will be recognized by those of skill in the art that various modifications, alternative constructions, and equivalents may be used without departing from the spirit of the disclosed embodiments. Additionally, a number of well-known processes and elements have not been described in order to avoid unnecessarily obscuring the present technology. It will be apparent to one skilled in the art, however, that certain embodiments may be practiced without some of these details, or with additional details. Accordingly, the above description should not be taken as limiting the scope of the technology.

It is noted that individual embodiments may be described as a process that is depicted as a flowchart, a flow diagram, or a block diagram. Although a flowchart may describe the method as a sequential process, many of the operations may be performed in parallel or concurrently. In addition, the order of the operations may be rearranged. A process may be terminated when its operations are completed, but could have additional steps not discussed or included in a figure. Furthermore, not all operations in any particularly described process may occur in all embodiments. A process may correspond to a method, a function, a procedure, a process, a subprocess, etc.

Where a range of values is provided, it is understood that each intervening value, to the smallest fraction of the unit of the lower limit, unless the context clearly dictates otherwise, between the upper and lower limits of that range is also specifically disclosed. Each smaller range between any stated value or intervening value in a stated range and any other stated or intervening value in that stated range is encompassed. The upper and lower limits of those smaller ranges may independently be included or excluded in the range, and each range where either, neither, or both limits are included in the smaller ranges is also encompassed within the technology, subject to any specifically excluded limit in the stated range. Where the stated range includes one or both of the limits, ranges excluding either or both of those included limits are also included.

As used herein and in the appended claims, the singular forms "a", "an", and "the" include plural references unless the context clearly dictates otherwise. Thus, for example, reference to "a dielectric material" includes a plurality of such materials, and reference to "the material layer" includes reference to one or more material layers and equivalents thereof known to those skilled in the art, and so forth.

Also, the words "comprise", "comprising", "include", "including", and "includes", "contains," "containing," etc., when used in this specification and in the following claims, are intended to specify the presence of stated features, integers, components, or steps, but they do not preclude the presence or addition of one or more other features, integers, components, steps, acts, or groups.

What is claimed is:

1. A method of filtering a fluid, comprising delivering a first fluid into a filtration device;
   flowing the first fluid across a front side of a filtration member located in the filtration device that includes a planar silicon or polysilicon membrane section having a thickness of less than about 1 µm and comprising a plurality of pores with each pore having a width of less than 100 nm;
   flowing a second fluid across a backside of the filtration member located in the filtration device that includes a support section comprising a substrate coupled with the membrane section, the substrate at least partially defining a cavity and a plurality of recesses, wherein:
   the cavity is located in the backside of the substrate and is in communication with the plurality of recesses, wherein the recesses are in communication with the defined pores,
   the plurality of recesses are defined by portions of the substrate such that each portion of the substrate located between any two recesses comprises a height of 50 µm or less,
   wherein the cavity comprises:

side walls having a first height; and the plurality of recesses defined by portions of the substrate having a second height, wherein the side walls having the first height slope inwardly towards the plurality of recesses and terminate at an angle greater than 90° into the portions of the substrate having the second height, wherein the first height is higher than the second height, and wherein the portions of the substrate having the second height have sides terminating at the membrane section at an angle of 90°, wherein the plurality of recesses are rectangular and repeat along a width of the cavity and along a length of the cavity, the plurality of recesses each comprising a length of 500 µm or less, a dielectric material disposed between the substrate and the planar membrane section, and wherein the dielectric layer defines a portion of the recesses, and the second fluid flows through the cavity to provide the second fluid to the recesses so that diffusive transport occurs across the membrane section between the first and second fluids to produce filtered first fluid; and transferring the filtered first fluid from the filtration device.

2. The method of claim 1, wherein the filtration device further includes a first channel in fluid communication with the membrane section of the filtration device, and a second channel in fluid communication with the support section of the filtration device.

3. The method of claim 1, further comprising:

flowing the first fluid through the first channel in a first direction of flow;

flowing a second fluid through the second channel in a direction of flow that is counter-current to the first direction of flow.

4. The method of claim 1, further comprising:

pumping the first and second fluid through the filtration device to maintain equal pressure across the membrane section of the filtration device.

5. The method of claim 1, further comprising:

incorporating an anti-coagulant into the first fluid prior to delivering the fluid to the filtration device.

6. The method of claim 1, wherein the plurality of pores are slit shaped.

7. The method of claim 1, wherein the portions of the substrate located between any two recesses comprise a height of about 20 µm or more.

8. The method of claim 1, wherein the plurality of recesses comprise a diameter of less than about 150 µm.

9. The method of claim 1, wherein the plurality of recesses comprise length by width measurements of about 100 µm by about 50 µm.

10. The method of claim 1, wherein the plurality of pores are slit shaped pores having a width of less than 15 nm.

11. The method of claim 1, wherein the plurality of slit shaped pores having a width of less than 10 nm.

12. The method of claim 1, wherein the cavity is at least 1 mm in length and width.

13. The method of claim 1, wherein the substrate comprises a silicon wafer.

14. The method of claim 1, wherein the plurality of recesses comprise length by width measurements of 100 µm by 50 µm or 250 µm by 50 µm.

* * * * *